US009480654B2

(12) United States Patent
Seiler et al.

(10) Patent No.: US 9,480,654 B2
(45) **Date of Patent: *Nov. 1, 2016**

(54) DRUG-DELIVERY SYSTEMS

(71) Applicant: EVONIK ROEHM GmbH, Darmstadt (DE)

(72) Inventors: Matthias Seiler, Griesheim (DE); Norbert Windhab, Hofheim (DE); Manfred Stickler, Seeheim-Jugenheim (DE); Hans-Ulrich Petereit, Darmstadt (DE)

(73) Assignee: EVONIK ROEHM GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/648,846

(22) Filed: Oct. 10, 2012

(65) Prior Publication Data

US 2013/0273163 A1 Oct. 17, 2013

Related U.S. Application Data

(63) Continuation of application No. 12/090,754, filed as application No. PCT/EP2006/010301 on Oct. 25, 2006, now Pat. No. 8,313,778.

(30) Foreign Application Priority Data

Oct. 25, 2005 (DE) ........................ 10 2005 051 366

(51) Int. Cl.

| | |
|---|---|
| ***A61K 38/00*** | (2006.01) |
| ***A61K 9/14*** | (2006.01) |
| ***A61K 9/16*** | (2006.01) |
| ***A61K 47/34*** | (2006.01) |
| ***A61K 47/48*** | (2006.01) |

(52) U.S. Cl.

CPC ............. *A61K 9/146* (2013.01); *A61K 9/1641* (2013.01); *A61K 47/34* (2013.01); *A61K 47/48192* (2013.01); *A61K 47/48207* (2013.01); *A61K 47/48238* (2013.01)

(58) Field of Classification Search

None

See application file for complete search history.

(56) References Cited

U.S. PATENT DOCUMENTS

| | | | | |
|---|---|---|---|---|
| 5,919,442 | A | 7/1999 | Yin et al. | |
| 6,426,362 | B1 * | 7/2002 | Miller et al. | 514/458 |
| 2002/0041898 | A1 * | 4/2002 | Unger et al. | 424/486 |
| 2003/0022821 | A1 * | 1/2003 | Svenden | C07K 14/79<br>514/2.5 |
| 2004/0013703 | A1 * | 1/2004 | Ralph et al. | 424/426 |
| 2013/0108662 | A1 | 5/2013 | Brock et al. | |

FOREIGN PATENT DOCUMENTS

| | | |
|---|---|---|
| CN | 1596123 | 3/2005 |
| EP | 1 352 657 | 10/2003 |
| EP | 1 352657 | 10/2003 |
| WO | WO 02 01172 | 2/2002 |
| WO | WO 03 051281 | 6/2003 |
| WO | WO2004-072153 | 8/2004 |
| WO | WO 2005055949 | 6/2005 |
| WO | WO2007-055561 | 5/2007 |

OTHER PUBLICATIONS van der Strate, B. W. A.; et al. "Synergy of bovine lactoferrin with the anti-cytomegalovirus drug cidofovir in vivo". Antiviral Research, 2003, v. 58, pp. 159-165.*
Diarra et al. Journal of Dairy Science, 2002, 85, 1141-1149.*
Chen et al. American Journal of Veterinary Research, 2004, 65(2), 131-137.*
Singh et al. American Journal of Physiol. Lung Cell Mol. Physiol., 2000, v. 279, L799-L805.*
Hayashida et al. American Journal of Physiology-Regulatory, Integrative and Comparative Physiology, 2003, v. 285, R306-R312.*
Leifert and Whitton, Mol. Therapy, 2003, v. 8, 13-20.*
Jeung et al. Journal of controlled Release, 2000, v. 63, 155-163.*
Wenzel et al. Apoptosis 2005; 10: 359-368.*
U.S. Appl. No. 13/988,829, filed May 22, 2013, Hartwig, et al.
German Search Report issued Aug. 2, 2006, in Patent Application No. 10 2005 051 366.2.
Joon Sig Choi, et al. "Enhanced transfection efficiency of PAMAM dendrimer by surface modification with L-arginine", Journal of Controlled Release 99, 2004, pp. 445-456.
Diarra, M. S.; Petitclerc, D.; Lacasse, P. J. Dairy Sci. 2002, v. 85, pp. 1141-1149.
Chen, P.-W.; Ho, S.-P.; Shyu, C.-L.; Mao. F. C. Am. J. Vet. Res., 2004, v. 65, pp. 131-137.
Singh, P. K.; Tack, B. F.; McCray, P. B., Jr.; Welsh, M. J. Am. J. Lung Cell Mol. Physiol., 2002, v. 279, pp. L799-L805.
Hayashida, K.-I.; Takeuchi, T.; Shimizu, H.; Ando, K.; Harada, E. Am. J. Physiol. Regul. Integr. Compo Physiol., 2003, v.285, pp. R306-R312.
International Search Report issued on Dec. 17, 2007 in Patent Application PCT/EP2006/010301.
Kolhe P. et al., Drug Complexation, In Vitro Release and Cellular Entry of Dendrimers and Hyperbranched Polymers•, International Journal of Pharmaceutics, vol. 259, pp. 143-160, XP008086791,2003.
Delong R. et ai, Charaterization of Complexes of Oligonucleotides With Polyamidoamine Starsurst Dendrimers and Effects on Intracellular Delivery•, Journal of Pharmaceutical Science, vol. 86, No. 6, pp. 762-764, XP008086807, 1997.
Office Action in Chinese Application No. 201410109016.6, dated Apr. 30, 2015. (w/English Translation).

* cited by examiner

*Primary Examiner* — Jeanette Lieb

(74) *Attorney, Agent, or Firm* — Oblon, McClelland, Maier & Neustadt, L.L.P.

(57) ABSTRACT

The invention relates to novel particulate drug-delivery systems based on a polymer support containing at least one linear, branched or cross-linked polymer in a fraction of over 50 percent by weight in relation to the total weight of the support. The system is characterized in that at least one signal substance for transport through a biological barrier and at least one active ingredient are stored, the support, signal substance and active ingredient having no covalent links and no active-ingredient specific and signal substance specific coordinative links between one another.

18 Claims, 5 Drawing Sheets

10μm

5μm

5μm

1μm

DRUG-DELIVERY SYSTEMS

This application is a Continuation of U.S. application Ser. No. 12/090,754, filed on Apr. 18, 2008, now allowed.

The invention relates to novel drug delivery systems based on polymeric carriers, in particular branched, crosslinked or dendritic carriers which comprise both at least one active ingredient and at least one signal substance, where carrier, active ingredient and signal substance are not specifically linked together or bindingly complementary.

One of the greatest problems in the medical treatment of diseases is represented by the targeted transport of active ingredients into the diseased target site, that is to say into a tissue, an organ or into the appropriate cells. Membranes are in this connection the most important barriers which shield the target site (site of action) from the active substances to be transported. A further problem is the degradation or derivatization of free active ingredients in the body. Such a metabolization reduces or often thwarts a targeted pharmacological effect of the active ingredients at the target site. In addition, incorrectly distributed or altered active ingredients may, especially if they have local or systemic toxicity, lead to unwanted side effects in the body.

A way which has already been tried for avoiding these disadvantages is the production of particulate active ingredient formulations, where the active ingredient is present bound in a polymeric shell or matrix (Nishiyama et al., Drug Discovery Today: Technologies (2005), 2(1), 21-26. Publisher: Elsevier B. V.). It is generally possible in this connection to distinguish pure volume carriers in which the active ingredient is enclosed in a type of polymeric container vesicle from chemically functionalized polymeric carriers in which individual ingredients, e.g. active ingredients or signal substances, are chemically bound to the functionalized carrier (matrix type).

Transport of the active ingredient into the diseased tissue takes place in the case of mere carrier/active ingredient formulations by simple release and diffusion (equilibration). In order to improve the guidance of particular active ingredients to the target, frequently signal substances are bound covalently or by coordination to the active ingredient or to the carrier, in which case the signal substance binds specifically to cell membranes of the diseased tissue and initiates the endocytotic described uptake of the active ingredient into the cell (e.g. WO 2005/084158, WO 2004/072153, Pitard, B. et al., Proceedings of the National Academy of Sciences of the United States of America (1999), 96(6), 2621-2626).

Although it is possible by attaching signal substances which initiate the endocytotic uptake of the active ingredient or of the particulate transport system to improve the guidance of the active ingredient to the target compared with purely diffusional uptake, new problems are also generated by the chemical functionalization of the carrier and by the attachment, covalently or by coordination, of the signal substance to the active ingredient.

Thus, in particular, optimization of active pharmaceutical ingredients is necessary in relation to their absorption, distribution, metabolism and excretion (ADME parameters) and in relation to their effect and toxicity. The attachment of a signal substance to the active ingredient often alters these properties, and the active ingredient may thereby be restricted in its pharmaceutical usability or even become useless. The binding of an active ingredient to a functionalized carrier usually gives rise to similar problems. In addition, carrier, signal substance and active ingredient frequently require extra functionalization in order to make appropriate specific attachment possible. Such chemically functionalized carriers and signal substances consequently allow only restricted carrier, signal substance, active ingredient combinations. Moreover, these drug delivery systems are complicated to produce, and the active ingredient must, if it is bound covalently or by coordination to the signal substance or the carrier, usually be chemically released at the target site. Attachment, covalently or by coordination, of a signal substance or carrier moreover results in a new chemical active ingredient requiring elaborate clinical testing.

The aim of the present invention was now to provide novel drug delivery systems which make targeted transport of the active ingredient through biological barriers possible and which eliminate at least some of the problems mentioned.

It has surprisingly been found in this connection that it is sufficient to use particulate drug delivery systems based on a branched or crosslinked polymeric carrier which are non-specifically aggregated both with the respectively employed active ingredients and with the signal substances used, without the need for attachment, covalently or by coordination, of the signal substance to the active ingredient or to the carrier.

Although the endocytotic and diffusive models which have been discussed to date have not been able to explain active ingredient transport through biological membranes without contradiction, it has tacitly been assumed to date that a specific linkage must exist between the active ingredient and the transport-initiating signal substance and between the signal substance and further fusion units or between the signal substance and the active ingredient-containing carrier for endocytotic transport of an active ingredient through a cell membrane, there being transport into the cell in the first case directly of the active ingredient and in the second case of the carrier with the active ingredient. However, according to the present invention, such a specific chemical coupling is precisely unnecessary. This active ingredient transport might in this case be attributable to a previously unknown mechanism for cellular uptake of active ingredients (FIG. 1).

Thus, the present invention relates to a drug delivery system based on a polymeric carrier, characterized in that at least one signal substance for transport through a biological barrier and at least one active ingredient are included, with carrier, signal substance and active ingredient showing no covalent linkages with one another.

Suitable carriers are linear polymers such as, for example, polylactides. However, preferred polymeric carriers comprise at least one branched or crosslinked polymer, because branched or crosslinked polymers are particularly suitable for mere aggregation of signal substance, active ingredient and carrier. The proportion of branched or crosslinked carrier polymers is preferably more than 10% by weight, in particular more than 50% by weight, based on the total weight of the carrier.

The signal substances and active ingredients are preferably in this case present dispersed or coacervated in the polymeric carrier. Particularly suitable for this purpose are dendritic or highly crosslinked polymers, and comb polymers. Of particular interest in this connection are nature-identical or nature-isomeric polymers.

Particularly preferred carriers are the highly branched, globular polymers which are also referred to in the specialist literature as "dendritic polymers". These dendritic polymers which are synthesized from multifunctional monomers can be divided into two different categories, the "dendrimers" and the "hyper-branched polymers". Dendrimers have a very regular, radially symmetric generation structure. They represent monodisperse globular polymers which, by comparison with hyperbranched polymers, are prepared in multistep syntheses. The structure is moreover characterized by three different areas:

the polyfunctional core which represents the centre of symmetry, various well-defined radially symmetric layers of a repeating unit (generation) and the terminal groups.

In contrast to the dendrimers, the hyperbranched polymers are polydisperse and irregular in terms of their branching and structure. Besides the dendritic and linear units, hyperbranched polymers also—in contrast to dendrimers—include linear units. One example each of a dendrimer (FIG. 2*a*) and of a hyper-branched polymer (FIG. 2*b*), constructed from repeating units which each have three bonding possibilities, is depicted diagrammatically in FIG. 2. Where the dendritic polymers used here have at least 3 repeating units per molecule, preferably at least 10 repeating units per molecule and particularly preferably at least 100 repeating units per molecule and very particularly preferably at least 200 repeating units per molecule or even better at least 400 repeating units per molecule, which in turn each have at least three, preferably at least four, bonding possibilities, where at least 3 of these repeating units, particularly preferably at least 10 and moreover preferably at least 20 are each linked via at least three, preferably via at least four, bonding possibilities to at least three, preferably at least four, further repeating units. The hyperbranched polymers normally have a maximum of 10000, preferably a maximum of 5000 and particularly preferably a maximum of 2500 repeating units.

In a preferred embodiment, the highly branched dendritic polymer has at least three repeating units each of which have at least three possible bonding possibilities, where at least three of these repeating units have at least two possible bonding possibilities.

In this connection, the term "repeating unit" preferably means a structure which is continually repeated within the hyperbranched molecule, e.g. linear, dendritic or terminal units as is defined in Seiler, Fortschritt-Berichte VDI, Series 3, No. 820 ISBN 3-18-382003-x and Gao, C. et al., Hyperbranched Polymers: from synthesis to application, Prog. Polym. Sci., 29 (2004) 183-275. The term "bonding possibility" preferably mean that functional structure within a repeating unit with which linkage to another repeating unit is possible. In relation to the examples described above of a dendrimer or hyperbranched polymer, the repeating unit is a structure having in each case three bonding possibilities (X, Y, Z):

The linkage of the individual bonding units with one another can take place by condensation polymerization, by free-radical polymerization, by anionic polymerization, by cationic polymerization, by group-transfer polymerization, by coordination polymerization, by ring-opening polymerization or by enzymatically catalysed polymerization.

Particularly preferred dendrimers are Starbust® polyamidoamine (PAMAM) dendrimers, polypropyleneimine dendrimers, polyethylene oxide-based dendrimers, polyether dendrimers, coated PAMAM dendrimers, e.g. with polylactide-co-glycolide coating, polylysine dendrimers, including polylysine-block-PEG-block-polylysine dendrimers, and polyaryl ethers. Such preferred dendrimers are described for example in Frechet, J. M. J. et al., Dendrimers and Other Dendritic Polymers, John Wiley & Sons Ltd., West Sussex, UK (2001); Malik, N. et al., Journal of Controlled Release 65, (2000), 133-148; Frey, H. et al., Reviews in Molecular Biotechnology 90 (2002) 257-267; Jikei, M. et al., Hyperbranched Polymers: a promising new class of materials, Prog. Polym. Sci., 26 (2001), 1233-1285.

Linear or hyperbranched carrier polymers which are preferred in this connection are polyesters, polyesteramides, polyethers, polyamides, polyethyleneimines, polyglycerols, polyglycolides, polylactides, polylactide-co-glycolides, polytartrates and polysaccharides. Polymers particularly preferred among these are the hyperbranched polyesters already commercially available under the trade name Boltorn® from Perstorp AB, the hyperbranched polyesteramides obtainable under the trade name Hybrane® from DSM BV Niederlande, the polyglycerols produced by Hyperpolymers GmbH, and the hyperbranched polyethyleneimines obtainable as Polyimin® from BASF AG.

Further preferred branched carrier polymers are polycaprolactones, copolymers such as poly(D,L-lactide-co-glycolides) and the polyester compounds produced by Degussa AG from the Dynapol®S and Dynacoll® product families.

Particularly preferred dendritic polymers are polymers having a molar mass between 1000 g/mol and 2 000 000 g/mol, particularly preferably between 2000 g/mol and 700 000 g/mol and very particularly preferably between 6000 g/mol and 100 000 g/mol, a melting point preferably between 0° C. and 150° C. and/or a melt viscosity of the preferred carrier polymers of less than 3.0 Pas, preferably less than 2.5 Pas, in particular less than 2.0 Pas, measured at 80° C. Hyperbranched polymeric carriers have in addition in particular a degree of branching of between 20% and 100%, preferably between 30% and 70% and/or a hydroxy number between 10 mg KOH/g and 600 mg KOH/g. The degree of branching of the dendrimers is preferably between 25% and 75%.

Further preferred carrier polymers are branched or crosslinked homo- or heteropolymers from carbohydrates (polysaccharides); from natural and artificial amino acids; from natural and artificial nucleic acids; from polyamines, from polyesters; from polyethers; from polyols, in particular polyvinyl alcohols, from polyolefins, in particular from polyisoprenes, polyethylenes, polypropylenes, polybutadienes or polystyrenes; from polyalkylene glycols, in particular from polyethylene glycols, from polyamides, from polyacetals, from polyacrylates; from polyacetates, in particular from polyvinyl acetates; from polyurethanes; from organosilicon polymers such as, for example, silicones; from epoxy resins, from polythiols or from polycarbonates.

Further preferred polymeric carriers are biocompatible and enzymatically degradable with a delay. Particular mention should be made in this connection of enzymatically degradable branched or crosslinked carrier polymers from the group of polycaprolactones, polyglycolides, polylactides, polylactide-co-glycolides, polytartrates or polyesters. Branched or crosslinked polysaccharides based on cellulose, pectin, amylopectin or dextrans are particularly preferred.

Particularly preferred crosslinked carrier polymers are hydrogels, especially dendritic hydrogels such as those described for example in Rueda, J. C., et al., Macromol. Chem. Phys. 2003, 204, 947-953; Hatice, K. C. et al., published online 24 Oct. 2003 in Wiley InterScience DOI 10.1002/app. 13125; Knischka, R. et al., Polymeric Materials: Science & Engineering 2001, 84, 945.

Polymeric carriers used in a particularly preferred embodiment are where possible left in the natural state or are near-natural and in particular are not further functionalized or derivatized. On the one hand, it is possible thus to ensure that no unwanted chemical reactions proceed with the active ingredients or the signal substances, thus possibly altering their pharmacological property profile, and, on the other hand, the risk of an allergic reaction to the drug delivery system is thus minimized.

In a preferred embodiment, the branched or crosslinked polymers have a content of at least 50% by weight, preferably of more than 75% by weight, based on the total weight of the carrier. It is additionally possible to admix further polymers, in particular also unbranched and uncrosslinked polymers of the polymer classes just mentioned with the carrier. In a particularly preferred embodiment, exclusively branched or crosslinked polymers are employed as carrier.

The proportion of the carrier in the claimed drug delivery system is preferably between 30% by weight and 99.5% by weight, preferably between 50% by weight and 98% by weight, based on the total weight of the particulate drug delivery system. Where formulations with highly active ingredients preferably have a proportion of more than 80% by weight to 99.5% by weight, in particular between 90% by weight and 99% by weight, carrier. Formulations with usual active ingredients by contrast have a preferred proportion of 55% by weight to 94.5% by weight, particularly preferably between 65% by weight and 94% by weight, carrier.

Signal substances mean in the context of the present invention all substances which are able to initiate a targeted transport of an active ingredient through a biological barrier. By this are meant in particular organism-specific peptides, including species-specific peptides, in particular mammal-specific, preferably human-specific peptides, which are able to have a transport-stimulating effect in relation to the biological barrier to be crossed. These include very generally stimulus signals of all biological, biomorphic or bioanalogous transduction domains (PTDs), especially receptor-binding peptides, d-analogous peptides, antibodies or fragments of said peptides or proteins. Substances found "de novo" (e.g. by Blast search in databases) such as, for example, haptens, receptor agonists and antagonists can furthermore also be employed as transport stimulus as signal substance. Preferred known signal peptides are selected from the group of "VP22" (protein from herpes simplex virus), "Antp" (having the amino acid sequence RQIKIWFQNRRMKWKK), "R9" (having the amino acid sequence RRRRRRRRR) and "Tat" (having the amino acid sequence YGRKKRRQRRR).

The signal peptide preferably employed is lactoferrin, in particular human or bovine lactoferrin, or a peptide comprising a lactoferrin fragment of at least 8 constitutive amino acids, with said peptide acting as cell-penetrating peptide (CPP).

In a preferred embodiment, said signal peptides comprise at least four cationic amino acids. The preferred cationic signal peptides have in particular a positive net charge at physiological pH values. In a further preferred embodiment, the signal substance employed is a peptide derived from lactoferrin, that comprises at least two cysteines or an appropriate analogue. In a particularly preferred embodiment, the signal peptide comprises a disulphide bridge formed from the two cysteine residues or an analogous linkage formed by a cysteine analogue. The two cysteines or analogues thereof are preferably separated from one another by 8 to 20 amino acids, in particular by 14 to 18 amino acids, particularly preferably by 16 amino acids. The two cysteines or analogues thereof may directly form the C-terminal and/or N-terminal end of the signal peptide or be located in the vicinity of the C- and/or N-terminal end. Such preferred bridge-stabilizing signal peptides ordinarily have a loop structure which have an increased stability toward enzymatic degradation, in particular toward protease degradation.

In a preferred embodiment, a human lactoferrin protein having the amino acid sequence SEQ ID No. 1 or a bovine lactoferrin protein having an amino acid sequence SEQ ID No. 2 is used.

In a further embodiment, the signal peptides derived from lactoferrin comprise a region with an alpha-helical conformation, preferably with a length of from 12 to 20 amino acids, or a region with a beta-pleated sheet conformation, preferably with a length of from 8 to 12 amino acids. Particularly preferred signal peptides have a helix-turn-sheet motif.

In a further preferred embodiment, the signal peptides derived from lactoferrin include from 8 to 60 amino acids, preferably 20 to 45 amino acids, particularly preferably 18 to 22 amino acids.

Particularly preferred signal peptides derived from lactoferrin are those having an amino acid sequence corresponding to the amino acids from position 20 to 64 of amino acid sequence SEQ ID No. 1.

It is further possible to use signal peptides whose N-terminal end is a sequence corresponding to amino acids of position 20 to 64 of amino acid sequences SEQ ID No. 1 or SEQ ID No. 2. Examples of such signal peptides are peptides having an amino acid sequence according to positions 20-711 corresponding to SEQ ID No. 1 or according to positions 20-708 corresponding to SEQ ID No. 2.

In a particularly preferred embodiment, a signal peptide is selected from the group of peptides having an amino acid sequence

```
                                   (SEQ ID No. 3)
KCFQWQRNMRKVRGPPVSCIKR,
                                   (SEQ ID No. 4)
CFQWQRNMRKVRGPPVSC,
                                   (SEQ ID No. 5)
FQWQRNMRKVRGPPVS,
                                   (SEQ ID No. 6)
FQWQRNMRKVR,
                                  (SEQ ID No. 29)
KCRRWQWRMKKLGAPSITCVRR
and
                                  (SEQ ID No. 30)
CRRWQWRMKKLGAPSITC
```

or a derivative thereof.

In a preferred embodiment, cell-penetrating peptides comprising an amino acid sequence as shown in SEQ ID No. 3, SEQ ID No. 4, SEQ ID No. 29 or SEQ ID No. 30 or a corresponding sequence with an identity of at least 40%, preferably of at least 50%, particularly preferably with an identity of more than 75% or better of more than 90%.

Signal peptides comprising an amino acid sequence with an identity of at least 40% to SEQ ID No. 3, SEQ ID No. 4, SEQ ID No. 29 or SEQ ID No. 30 are preferably characterized by exchange and/or deletion of from 1 to 13 amino acids by comparison with SEQ ID No. 3 or SEQ ID No. 29, or of from 1 to 10 amino acids by comparison with SEQ ID No. 4 or SEQ ID No. 30. Where sequences which through the exchange one or of more amino acids by homologous amino acid are of increased interest.

Peptides which include an amino acid sequence as shown in SEQ ID No. 3, SEQ ID No. 4, SEQ ID No. 29 or SEQ ID No. 30 or a corresponding sequence with an identity of at least 40% consist of at least 8 amino acids (for signal peptides derived from SEQ ID No. 3 or SEQ ID No. 29) or of at least 9 amino acids (for signal peptides derived from SEQ ID No. 4 or SEQ ID No. 30). The signal peptides preferably have from 10 to 45 amino acids, particularly preferably 14 to 25 amino acids.

Exchange of a homologous amino acid preferably means exchange of an amino acid by another one of the same group. In this connection, the amino acids can be divided into hydrophobic amino acids (including the aliphatic amino acids), aromatic amino acids, cationic and anionic amino acids, neutral amino acids, sulphur-containing amino acids and heterocyclic amino acids. Hydrophobic amino acids are preferably glycine, alanine, valine, leucine and isoleucine, aromatic amino acids are preferably phenylalanine, tyrosine and tryptophan, ionic amino acids are preferably cationic amino acids such as lysine, arginine, histidine, and anionic amino acids such as aspartate and glutamate, neutral amino acids are preferably serine, threonines, asparagine, glutamine and methionine, sulphur-containing amino acids are preferably cysteine and methionine and heterocyclic amino acids are preferably proline and histidine.

Preferred signal peptides as shown in SEQ ID No. 3, SEQ ID No. 4, SEQ ID No. 29 or SEQ ID No. 30 or a corresponding sequence with an identity of at least 40% have a cationic charge, in particular through at least four cationic amino acids which are located within SEQ ID No. 3, SEQ ID No. 4, SEQ ID No. 29 or SEQ ID No. 30. A further preferred feature of said signal peptides is the presence of at least two cysteine residues or cysteine analogues able to form a disulphide bridge or a bridge analogous thereto. The two cysteines or analogues thereof enclose at least 6, preferably between 12 and 43 amino acids.

In a further preferred embodiment are derivatives of peptides having an amino acid sequence as shown in SEQ ID No. 3-6, where the methionine residue is replaced by an amino acid selected from the group comprising valine, isoleucine, norvaline, leucine and norleucine. Examples of such peptides are peptides having an amino acid sequence:

```
                        (SEQ ID No. 7)
KCFQWQRNVRKVRGPPVSCIKR,

                        (SEQ ID No. 8)
KCFQWQRNIRKVRGPPVSCIKR,

                        (SEQ ID No. 9)
KCFQWQRNXRKVRGPPVSCIKR,
where X is norvaline,

                       (SEQ ID No. 10)
KCFQWQRNLRKVRGPPVSCIKR,

                       (SEQ ID No. 28)
KCFQWQRNXRKVRGPPVSCIKR,
where X is norleucine,

                       (SEQ ID No. 11)
CFQWQRNVRKVRGPPVSC,

                       (SEQ ID No. 12)
CFQWQRNIRKVRGPPVSC,
```

-continued

```
                       (SEQ ID No. 13)
CFQWQRNXRKVRGPPVSC,
where X is norvaline,

                       (SEQ ID No. 14)
CFQWQRNLRKVRGPPVSC,

                       (SEQ ID No. 15)
CFQWQRNXRKVRGPPVSC,
where X is norleucine,

                       (SEQ ID No. 16)
FQWQRNVRKVRGPPVS,

                       (SEQ ID No. 17)
FQWQRNIRKVRGPPVS,

                       (SEQ ID No. 18)
FQWQRNXRKVRGPPVS,
where X is norvaline,

                       (SEQ ID No. 19)
FQWQRNLRKVRGPPVS,

                       (SEQ ID No. 20)
FQWQRNXRKVRGPPVS,
where X is norleucine,

                       (SEQ ID No. 21)
FQWQRNVRKVR,

                       (SEQ ID No. 22)
FQWQRNIRKVR,

                       (SEQ ID No. 23)
FQWQRNXRKVR,
where X is norvaline,

                       (SEQ ID No. 24)
FQWQRNLRKVR,

                       (SEQ ID No. 25)
FQWQRNXRKVR,
where X is norleucine.
```

In a further preferred embodiment, the signal peptides also include those derivatives comprising a linker group, preferably selected from the group of thioesters, where the linker group replaces the disulphide bridge. It is moreover possible to incorporate into the peptide linker groups which structurally and functionally replace the disulphide bridge but are not subject to reductive cleavage. Examples of such linker group are ethylene bridges (JACS, 1985, 107, 2986-2987, Bioorg. Med. Chem. Letter 1999, 9, 1767-1772, J. Med. Chem. 2002, 45, 1767-1777), thioether bridges (Yu et al. Tetrahedron Lett. 1998, 39, 6633-6636), carbonyl bridges (Pawlak et al., J. Pept. Sci. 2001, 7, 128-140), longer aliphatic bridges, in particular having up to 10 carbon atoms (Tetrahedron Lett. 2001, 42, 5804). A further possibility is also to replace a cysteine residue by other residues such as, for example, homoserine (Yu et al., Tetrahedron Lett. 1998, 39 6633-6636).

Said peptidic signal substances may also be radio-labelled, preferably with a radio-labelled amino acid, in particular with a tritium-labelled amino acid. The signal substances may furthermore be modified with detectable groups, such groups preferably being selected from the group of fluorophores, of radioactive tracers and haptens, the hapten biotin being particularly suitable.

It is possible through the use of human signal substances, in particular of cell-penetrating peptides derived from lactoferrin, in particular to minimize allergic reactions directed against the drug delivery system. The peptides derived from lactoferrin further show a high efficiency in cell penetration both in relation to the amount of peptide or peptide formulation taken up in the cell, and in relation to the time required for uptake. It is further advantageous that the peptides, formulations or ingredients of the formulations which are taken up are transported into the cytoplasma of the cell.

The signal peptides derived from lactoferrin are of interest in particular in relation to transport of active ingredients through the intestinal epithelium, in which case the active ingredient is transported with high efficiency into the epithelial cells and is subsequently delivered into the bloodstream. The signal peptide can also be masked for targeted transport of active ingredients, e.g. into tumour cells. The masked peptide can then be cleaved, by a proteolytic cleavage, e.g. by proteases which are released by tumour cells, into its functional cell-penetrating form (analogous to Jiang, T. et al., Proc. Natl. Acad. Sci., USA, 17867-17872, 2004).

Said signal peptides can further be in a form derivatized by usual methods. Particular mention should be made in this connection of C-terminally acetylated or amidated peptides, which are often distinguished by good stability under physiological conditions. However, unmodified signal peptides are preferably used.

The loading of the carrier with a signal substance typically takes place with a quantity between 0.5% by weight and 20% by weight, preferably between 1% by weight and 10% by weight, based on the total weight of the particulate drug delivery system.

It is furthermore known in particular from "antisense" technology that ionic compounds, nucleic acids, nucleic acid fragments, nucleic acid conjugates and nucleic acid analogues can enhance membrane transports, i.e. pure or chemically modified fragments are likewise employed as supplementary stimulus.

Since no specific coupling, either of the active ingredients or of the signal substances, takes place, the loading of the polymeric carrier is not restricted in relation to the active ingredients and signal substances which can be used to produce the particulate drug delivery systems. However, the transport systems described herein are to be regarded as particularly advantageous for active ingredients or active ingredient mixtures which must be protected from chemical or enzymatic degradation during transport to the target site and which, to avoid side effects, must be released only at the target site. Consequently, the described drug delivery systems are particularly suitable for transporting pharmaceutically effective peptides or proteins. Such active ingredients are for example pharmaceutical proteins or proteo active ingredients, such as, for example, antibodies, peptide hormones, receptors or peptidic ligands thereof or enzymes. Examples thereof which may be mentioned are the α1-protease inhibitor, eglin, elastase, α1-antitrypsin (emphysemas), antithrombin (anticoagulant), angiotensinase (high blood pressure), factor VII, VIII, IX, X, fibrinogen, thrombin, plasminogen activator inhibitor (coagulation disorders), immunoglobulins (passive immunization), gancyclovir, acyclovir, interferons (viral infections, tumour therapy), tumour necrosis factor, cachectin, dihydrofolate reductase, lymphotoxin, interleukins, tumour suppressor proteins such as, for example, p53 (cancer), plasmin, urokinase, hirudin, streptokinase, urokinase, tissue plasminogen activator, protein C, protein S (thrombolysis), phospholipase $A_2$, uromodulin, Tamm-Horsfall protein (inflammations), insulin (diabetes), trypsin inhibitor (pancreatitis), lysozyme, thymopoietin, peptide antibiotics (bacterial infections), erythropoietin (anaemia). However, the drug delivery systems described herein are not confined to such active ingredients; it is also possible to employ low molecular weight active ingredients (small molecules) such as, for example, many antiviral substances, hepatotherapeutic substances, neuroprotective substances, immunotherapeutics and -suppressants, low molecular weight active ingredients for cardiovascular disorders or cancer, analgesics, low molecular weight antiinflammatory, antibiotic and antimicrobial active ingredients and low molecular weight hormones, or macromolecular active ingredients such as, for example, nucleic acid fragments or nucleic acids (genomic DNA, cDNA, mRNA, siRNA, antisense oligonucleotides etc.). Examples of low molecular weight active ingredients are nucleoside analogues, β-interferons, α-lipoic acid, peptide analogues, enzyme or receptor inhibitors, agonists and antagonists, prostaglandins, steroids, cytostatics and heterocyclic antibiotics. It is also possible in particular to employ active ingredients in the form of their prodrugs.

One advantage of the present transport particles is that it is also possible to incorporate two or more active ingredients, in particular also having different physical properties, such as, for example, different hydrophilicity, together in one formulation. A pharmacological classification in this regard is provided by the BCS system which was developed by the FDA and divides active pharmaceutical ingredients into four different classes. The particles described herein are particularly suitable precisely for including active ingredients from different classes in one transport system.

The loading of the carrier with an active ingredient typically takes place with an amount between 0.001% by weight to 50% by weight based on the total weight of the particulate drug delivery system. Where active ingredients having a high activity are preferably present in an amount between 0.01% by weight and 1% by weight, particularly preferably below 0.1% by weight. Other active ingredients are generally employed in an amount between 1% by weight and 30% by weight, preferably between 5% by weight and 25% by weight.

The active ingredient content in the particulate drug delivery system is chosen for pharmaceutical formulation so that preferably between 0.1 mg and 100 mg of active ingredient per kg of a patient's body weight are reached. In the case of active ingredients having high activity, such as, for example, hormones, lower dosages also suffice.

A particularly preferred feature of the signal substances and active ingredients used here is that they are unmodified. "Unmodified" means in the context of the present invention that the signal substance or the active ingredient is not derivatized with any additional functional groups or linkers in order to make coordination or covalent bonding to the carrier or with one another possible.

The term "biological barrier" means in the context of the present invention besides the cell membrane in general in particular also epithelial and endothelial cell layers. Consequently, the term biological barrier also covers organ and tissue barriers such as, for example, the blood-brain barrier or the intestinal epithelium. Where vascularization ensures good pharmacokinetic further transport (active ingredient suction) after the barrier has been crossed.

It is crucial for constructing the particulate drug delivery systems according to the invention that both active ingredients and signal substances are in non-specific aggregation with the branched or crosslinked polymeric carrier, that is to say do not enter into any covalent bonding with one another. The term covalent bonding also includes coordination bindings where the bonding electron pair is provided by one binding partner to a defined electron pair acceptor. The term coordination binding does not include any non-specific bindings which are unstable and nonselective under physiological conditions. Specific coordination bindings are represented for example by complexations such as epitope bindings or haptamer-like or aptamer-like bindings. Linkages also generally designated as host-guest bindings are to be regarded as a complex-forming binding. Such coordination bindings are distinguished by their stability and selectivity of the binding under physiological conditions. Non-selective, non-specific bindings in the sense of the present invention are polar interactions or lipophilic interactions and Van der Waals interactions which usually have a binding enthalpy of less than 50 kJ/mol or of less than 20 kJ/mol (depending on the considered radical which is available for such a binding). In the particulate transport systems described herein, by contrast, both the signal substances and the appropriate active ingredients are preferably simply dispersed or coacervated in the polymeric carrier material.

Drug delivery systems configured in this way have diverse advantages over conventional active ingredient formulations. Thus, the active ingredients and the signal substances can be employed without chemical modifications, thus retaining their properties, in particular in relation to their effect and in relation to the ADME parameters. It is furthermore possible also to employ natural branched or crosslinked polymeric carriers or ones composed of naturally occurring monomers. It is thus possible to obtain well-tolerated particulate drug delivery systems which should in particular also be advantageous for avoiding allergic reactions. The drug delivery systems according to the invention are also easier to produce because neither additional functionalization of individual components nor a specific linkage between carrier, signal substance and/or active ingredient is necessary. It is thus additionally possible simply to combine together different signal substances and active ingredients without a new active ingredient resulting, as would be the case for example on covalent linkage of the Tat protein (signal substance) with a p53 protein (active ingredient) (Tat-p53 fusion protein). In addition, it is also unnecessary for the active ingredient to be released, e.g. by a proteolytic or enzymatic elimination from the carrier and/or the signal substance. A further advantage of the described drug delivery systems is to be regarded as the fact that different signal substances and active ingredients can be formulated together in one transport system. The amounts of the signal substances and active ingredients with which the transport particles are loaded can also be chosen freely and can thus be adapted without difficulty to the respective indication.

In particular, through the use of dendritic carrier polymers it is possible to adjust via the type and number of functional groups, in particular of polar groups, in the carrier the loading concentration of the particles with an active ingredient and a signal substance, and it is moreover possible to achieve unusually high loading concentrations of more than 20% by weight of active ingredient and signal substance based on the total weight of the particles. In addition, the amount of active ingredient released per unit time can also be controlled via the number of functional groups.

In a preferred embodiment, the peptides derived from lactoferrin are incorporated as signal substances into the claimed drug delivery system, utilizing for the formulation negatively charged or readily polarizable carriers. An alternative possibility is also to employ carriers with a net positive charge, using a negatively charged formulation aid, such as, for example, by means of nucleic acid fragments.

Consequently, drug delivery systems of particular interest comprise a) a cell-penetrating signal peptide (CPP) derived from lactoferrin,
b) an active pharmaceutical ingredient and
c) a polymeric carrier composed of branched or crosslinked homo- or heteropolymers of carbohydrates (polysaccharides); of polyesters; of polyethers; of polyols, of polyolefins, of polyalkylene glycols, of polyamides, of polyacetals, of polyacrylates; of polyacetates, of polyurethanes, of organosilicon polymers, of epoxy resins, of polythiols, of polycarbonates, of polycaprolactones, of polyglycolides, of polylactides, of polylactide-co-glycolides or of polytartrates.

Such formulations are particularly suitable for transcellular transport of active pharmaceutical ingredients through the intestinal epithelium. Accordingly, combination of lactoferrin-derived CPPs and hepatotherapeutics such as, for example, certain cytostatics, nucleoside analogues or α-lipoic acid, interferon, lamivudine, corticoids, azathioprine, chlorambucil, colchizine, methotrexate, ursodeoxycholic acid, naloxone, amphotericin B, fluconazole, albendazole, is particularly preferred.

The particulate drug delivery systems can be administered for example by the oral, pulmonary, sublingual, buccal, nasal, ocular or gastrointestinal route. Of particular interest in this connection are in particular the oral and intravenous administration form. For this purpose, the transport particles can be encapsulated without loss of function additionally with commercially available pharmaceutical substances, such as Eudragit® for example.

The particulate drug delivery systems can be produced by various methods. In this connection, the coacervation method besides spray drying, the high-pressure method with compressed gases and the solvent evaporation has proved to be a preferred method. It is possible in principle for the active ingredient and signal substance to be formulated together or in separate operations to the drug delivery systems of the invention.

Coacervation is a forced phase separation to precipitate colloids and to produce particles. This can be induced by various external stimuli such as temperature, pH, salt solutions or nonsolvents. Finally, the resulting particles are consolidated by heat, crosslinking, solvent removal or drying. The coacervation method is very versatile and can be carried out with various polymers. It is moreover possible for the wall thickness and the size of the particles, and the degree of loading of an (active) active ingredient, to be varied without restriction. It is moreover possible for the release profile of the encapsulated active ingredient to be adjusted as desired. The coacervation method is a very efficient method for producing particulate formulations because it allows a high yield, a high loading rate and a good reproducibility.

A distinction is made between simple and complex coacervation, and between aqueous and organic phase separation (Arshady, R. Microspheres and microcapsules, a survey of manufacturing techniques, Part II, Coacervation, Polymer Engineering and Science, 30(15), 905, 1990). In simple coacervation there is use of one colloidal component, e.g. gelatin, and in complex coacervation there is use of two oppositely charged colloidal components, e.g. gelatin and gum arabic. The coacervation principle consists of for example converting an aqueous gelatin solution by adding ethanol into a two-phase system consisting of a gelatin-rich (coacervate) and a gelatin-poor phase. This is very similar to a polymer fractionation, although in this case microparticles with an average size of 2-5000 μm are produced by the action of shear forces.

Production of microcapsules by coacervation can be divided into three steps: (1) generation of three immiscible phases, (2) deposition of the colloid as capsule shell and (3) consolidation of the capsule shell. The three immiscible phases consist of an external medium, a core material and the capsule shell material. The capsule shell material is dissolved in the external medium, and the core material is dispersed therein. When an external stimulus (temperature, pH, electrolytes) acts, the capsule shell material becomes insoluble in the external medium and is deposited at the interface with the dispersed core material. After filtration, the capsule shell is finally hardened by the action of heat, crosslinking or solvent removal or dried by spray drying or freeze drying.

The particulate active ingredient formulation is dried particularly advantageously by washing the particles in a particularly volatile solvent (e.g. ethanol, propanol, acetone, dichloromethane) with subsequent drying in a vacuum, plate or tumble dryer. Alternatively, it might also take place by spray or freeze drying. The solvent-rich phase which remains on removal of the particles can be recycled on a relatively large scale.

Microparticles can be loaded with an (active) ingredient, i.e. that the core material corresponds to this active ingredient. This may involve hydrophobic or hydrophilic substances, leading to the need to use an aqueous or an organic phase separation. In the case of aqueous phase separation it is possible for hydrophobic substances to be enclosed/encapsulated. Conversely, an organic phase separation is required for hydrophilic substances, i.e. the colloid is dissolved in the organic phase and, after the action of an external stimulus, accumulates at the interface with the hydrophilic substance. The terms aqueous and organic coacervation thus stand in each case for water- and oil-soluble colloids. The loading of the microcapsules with the signal substance and active ingredient is 0.5-70% by weight and the release of the enclosed substance can be initiated by various mechanisms: diffusion, dissolving of the capsule shell material, enzymatic degradation, etc. The following capsule shell materials are preferably used in simple coacervation: carboxymethylcellulose, nitrocellulose, polyvinyl alcohol, polyurethanes, shellac, carrageenan, alginates, gelatin, albumin, collagen, cellulose acetate, phthalates, ethylcellulose, polyglycerols, polyesters, Eudragits®, etc. In the case of complex coacervation, preferably the following combinations with gelatin are used: gelatin with gum arabic, Carbopol or pectin.

A further possibility for producing the particulate active ingredient formulations according to the invention is represented by high-pressure processes with compressed or supercritical fluids (Gamse et al., in Chemie Ingenieur Technik 77 (2005) 669-680; McHugh and Krukonis in "Supercritical Fluid Extraction: Principles and Practices", Stoneham M A 1986, Fages et al., Powder Technology 141 (2004) 219-226 and Bungert et al., Ind. Eng. Chem. Res., 37, (1997) 3208-3220).

The best-known methods for particle production with compressed gases are the GAS (Gas AntiSolvent) process, the PCA (Precipitation with a Compressed fluid Antisolvent) process, the PGSS (Particles from Gas Saturated Solutions) process and the RESS (Rapid Expansion of Supercritical Solutions) process. These methods are explained briefly below.

In the GAS process, a solution which comprises polymer, active ingredient, signal substance and solvent is introduced into an autoclave at constant temperature and then exposed to a gas as nonsolvent, so that the polymer and the active ingredient precipitate as fine particles. In this case, mixing of the solution/suspension by means of a stirrer is sensible in order to prevent agglomeration of the particles.

The signal substance and active ingredient molecules may during the precipitation be bound in the polymer matrix or be present as core (reservoir) around which a polymeric coating has formed. A suspension is then formed and can be fractionated by filtration. Solvent residues can be extracted by washing the particles in a supercritical fluid. Besides the possibility of carrying out the process at low and thus active ingredient-sparing temperatures, particularly important is the influencing of the kinetics of the phase transition, that is of the particle formation. The particle size distribution can also be chosen by controlling the supersaturation by the time course and the intensity of the addition of gas. In a first step, the phase separation is initiated and there is formation of crystallization nuclei in the form of droplets of the resulting polymer-rich phase, of the later microparticles. It is now important not to allow these droplets to coalesce and grow, but to ensure that the solvent is extracted as quickly as possible out of these drops. The resulting particles then have small diameters (Gamse et al., Chemie Ingenieur Technik 77 (2005) 669-680 and Bungert et al., Ind. Eng. Chem. Res., 37, (1997) 3208-3220). The particle distribution and particle size can be adjusted by targeted variation of these two steps.

The PCA process or else SEDS (Solution Enhanced Dispersion by Supercritical Fluids) process optimizes the two limiting quantities of the GAS process, namely the rate of pressure build-up as initiator of particle formation and the transport of matter in order to remove the solvent out of the drops (Gamse et al., in Chemie Ingenieur Technik 77 (2005) 669-680; Fages et al., Powder Technology 141 (2004) 219-226 and Bungert et al., Ind. Eng. Chem. Res., 37, (1997) 3208-3220). The signal substance-active ingredient-polymer solution from the autoclave is in this case compressed and brought into contact in an injection nozzle with the supercritical gas and sprayed together in the precipitation unit. In a final washing step, the solvent is removed from the particles by extraction with the supercritical fluid. A high rate of pressure build-up can be achieved through the short contact time by bringing solution and supercritical fluid together shortly before the spraying step in the nozzle. As already mentioned above, the result thereof is a high supersaturation of the polymer-active ingredient-signal substance solution. It is possible in this way to achieve homogeneous distributions and small particle sizes, since the initiated phase separation is followed, through the spraying, by a fine dispersing in which an improved transport of matter of the solvent into the compressed or supercritical gas can take place owing to the high specific surface area of the polymer solution drops. It is possible through the super-critical spray drying to combine displacement crystallization and crystallization by solvent evaporation.

The PGSS process differs fundamentally from the high-pressure processes described above, because it makes do without a (frequently toxic) solvent for the polymer. As described by Weidner in WO 95/21688, Gamse et al. in Chemie Ingenieur Technik 77 (2005) 669-680, Fages et al., Powder Technology 141 (2004) 219-226 and Bungert et al., Ind. Eng. Chem. Res., 37, (1997) 3208-3220, this process makes use of the effect of lowering the glass transition temperature of a polymer by the supercritical fluid. The polymer is molten in the supercritical fluid, and the active ingredient is dispersed in the solution. During this, the viscosity of the polymer melt also decreases. The polymer-gas melt with the dispersed active ingredient and signal substance is decompressed in the precipitation unit through a nozzle, with the nozzle additionally also possibly being supplied with supercritical gas. As a result of the reduction in temperature through the Joule-Thomson effect, the solution cools, and the polymer precipitates as fine powder. The particles can be removed from the gas stream in a cyclone or a downstream electrofilter. The different size fractions can be fractionated in this way. The active ingredient can be dispersed in the polymer matrix owing to the melting of the polymer. The decompression in the nozzle results in fine, monodisperse particles.

The RESS process resembles the PGSS process because no organic solvent is used in this process either. As described by Gamse et al. in Chemie Ingenieur Technik 77 (2005) 669-680, Fages et al., Powder Technology 141 (2004) 219-226 and Bungert et al., Ind. Eng. Chem. Res., 37, (1997) 3208-3220, firstly the polymer is dissolved in a high-pressure autoclave. The active ingredient and the signal substance are either likewise dissolved or dispersed with a stirrer. In the case of loaded microparticles, homogeneous dispersion of the active ingredient and of the signal substance in the melt is extremely important because ultimately the size of the active ingredient molecules represents the crucial limitation for the size of the microparticles (Gamse et al., Chemie Ingenieur Technik 77 (2005) 669-680; Fages et al., Powder Technology 141 (2004) 219-226 and Bungert et al., Ind. Eng. Chem. Res., 37, (1997) 3208-3220). The supercritical solution is sprayed in a precipitation unit at ambient pressure. The supersaturation of the solution or of the droplets on decompression takes place with a very much greater speed by comparison with the methods described above. Owing to the decompression, the density of the supercritical fluid and thus also the dissolving power falls in a very short time to gas-typical values. Nucleus formation and transport of matter take place in direct succession in this process and are optimized many times over by comparison with the other methods (Gamse et al., Chemie Ingenieur Technik 77 (2005) 669-680; Fages et al., Powder Technology 141 (2004) 219-226 and Bungert et al., Ind. Eng. Chem. Res., 37, (1997) 3208-3220).

Particulate drug delivery systems with a preferred particle diameter of less than 900 μm, preferably of less than 500 μm, can be obtained easily with the methods described. It is also possible with the described methods to produce drug delivery systems with a particle diameter of between 100 nm and 100 μm, the particles normally employed having a particle diameter of between 500 nm and 10 μm.

The active ingredient and signal substance loading of the carrier by coacervation or active ingredient and signal substance dispersion in a carrier polymer melt or a carrier polymer-rich solution preferably takes place in a temperature range between −30° C. and +100° C., particularly preferably between 0° C. and 60° C. The pressure during these processes is preferably between 0.1 mbar and 20 bar, particularly preferably between 1 mbar and 10 bar.

The alternative production of the active ingredient formulation according to the invention by spray drying, the GAS (Gas AntiSolvent) process, the PCA (Precipitation with a Compressed fluid Antisolvent) process, the PGSS (Particles from Gas Saturated Solutions) process and the RPESS (Rapid Expansion of Supercritical Solutions) process preferably takes place in the temperature range between −30° C. and +150° C., preferably between 0° C. and 100° C. and with system pressures of between 0.1 mbar and 250 bar, preferably between 1 bar and 180 bar.

Suitable solvents which should be mentioned for the described production methods are in particular water, alcohols such as, for example, ethanol or isopropanol, compressed $CO_2$, compressed propane, tetrahydrofuran, toluene, acetone, benzoyl peroxide, aqueous HCL solution, hexane, acetic acid, ethanediol, dichloromethane, dichloroethane and ionic liquids.

The encapsulation of the particulate drug delivery systems provided in this way, in particular for oral availability in principle, is possible without loss of function using commercially available pharmaceutical substances such as, for example, with EUDRAGIT® (Degussa AG, DE).

If special variants of the coacervation method or special coating methods (spray drying, Brace microsphere process, coaxial nozzle, fluidized bed coating) are employed, the active ingredients and signal substances can be enveloped or coated with one or more carrier polymers in a plurality of layers. Thus, for example, the signal substances can be incorporated in the outer layer, and the active ingredients in the inner layer, so that first the signal substance and then the active ingredient is released. It is additionally possible for a plurality of different active ingredients also to be aggregated in different particle layers.

When active pharmaceutical ingredients are incorporated into pharmaceutical formulations, e.g. using the methods just described, always more specific requirements must be met by the stability of the active ingredient formulations, the property profile of the carrier polymer, the release trigger and the release kinetics. This is because the active ingredients occasionally show a sensitive reaction to their environment (enzymatic degradation, temperature, pH changes), are insoluble or are non-lipophilic. The particulate drug delivery systems produced with these methods using the linear or branched or crosslinked polymeric carriers described above show a particularly high stability, thus making it possible in particular for toxic, sensitive, reactive or unstable active pharmaceutical ingredients to be released in a controlled manner and stabilized together with the signal substances. If branched or crosslinked carrier polymers, preferably dendritic polymers and particularly preferably polyester group-containing hyperbranched polymers, hyperbranched polyglycerols, polysaccharides or PAMAM dendrimers as carrier materials for biologically active active ingredients and signal substances it is possible for the described disadvantages to be diminished or entirely eliminated.

Furthermore, in particular the dendritic carrier polymers, probably because of their melt and solution viscosities which are comparatively low for polymers, the encapsulation methods can be operated with distinctly reduced amounts of solvent or compressed gases. The dendritic polymer acts in this case itself as solvent/dispersant. The reduced occurrence of solvent makes the production of the particulate transport systems safer, in particular the release of vapours which are explosive or harmful to health is distinctly reduced.

Controlled release of active ingredient can be influenced in particular by the thickness of the carrier polymer layer which surrounds the active ingredient and the signal substance, the nature and number of the functional groups in the carrier polymer and by the type of encapsulation method. The release period becomes longer as the carrier polymer shell becomes thicker. The thickness of the carrier can be achieved, besides variation of the process parameters (pH, temperature, solvent), in particular by changing the polymer concentration in the initial mixture. It is possible through the use of dendritic polymers as carrier to increase the loading of the carrier with active ingredients and signal substances to up to 70% by weight, so that particularly long release times with large amounts of active ingredient released can be achieved. Besides the thickness of the carrier polymer shell, the release period is decided by the degree of functionalization and by the hydroxy number. If the active ingredients are to be released in polar media, the release becomes slower when fewer free polar groups, e.g. OH groups, are present in the carrier polymer. The number of free OH groups can in turn be influenced by esterification with fatty acids.

Release of the signal substances and active ingredients from the particulate drug delivery system takes place by various mechanisms such as, for example, by enzymatic degradation of the carrier polymer, by hydrolytic processes, pH changes or temperature changes. Enzymatic degradation of the carrier is of particular interest for the targeted release of pharmacological active ingredients. Particularly suitable polymeric carriers in this regard are ester group-bearing polymers, especially branched or crosslinked, preferably dendritic polyesters.

The particulate drug delivery systems may further comprise conventional excipients such as, for example, stabilizers, surfactants, oils, waxes, plant, yeast or algal extracts, amino acids, amino acid derivatives, vitamins and derivatives thereof, bioactive lipids such as cholesterol, ceramides, pseudoceramides, antioxidants, preservatives, colorants and pigments.

EXEMPLARY EMBODIMENTS

Figure 1A:
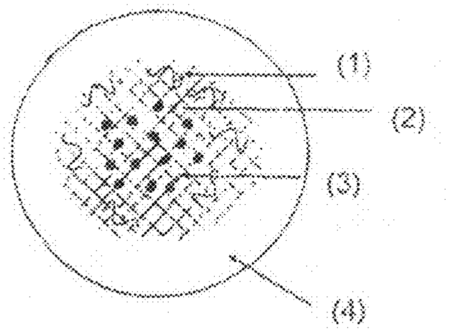
FIG. 1*a* shows by way of example a carrier-active ingredient-signal substance aggregate consisting of a non-specifically incorporated, unmodified barrier signal substance (1), e.g. the Tat protein, of a non-specifically incorporated, unmodified active ingredient (2), with the signal substance and the active ingredient being coacervated in two layers with a branched polymeric carrier (3). The active ingredient formulation is additionally surrounded by an oral-digestive layer (4), e.g. of Eudragit®.
Figure 1B:
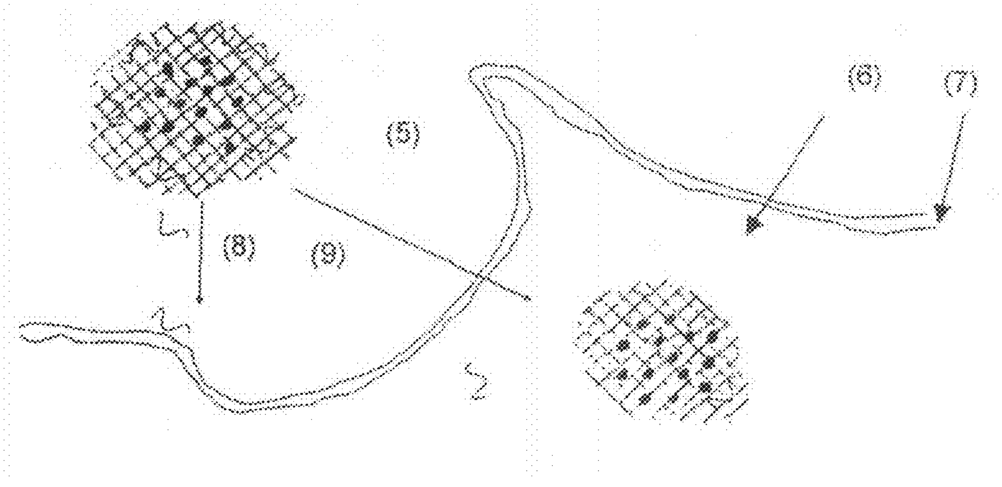
FIG. 1*b* shows the release of the signal substance (8) in the extracellular matrix (5), whereby uptake (9) of the transport system through the cell membrane (7) into the cytoplasm (6) takes place.
Figure 1C:
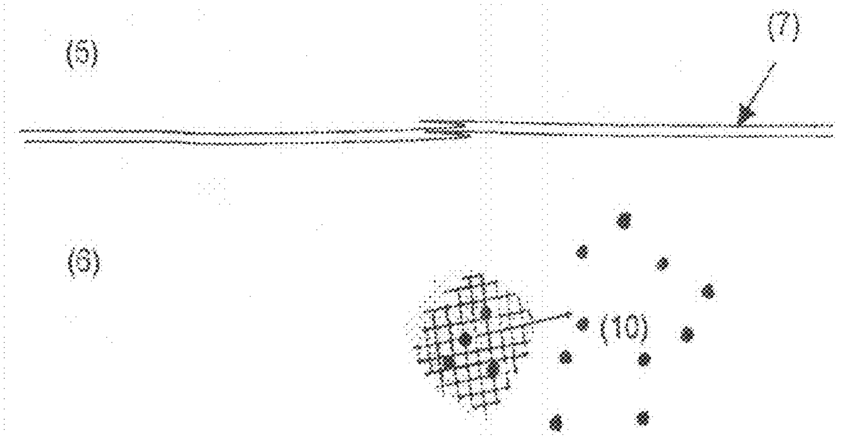
FIG. 1*c* then shows the following release (10) of the active ingredient in the cell.
Figure 2A:
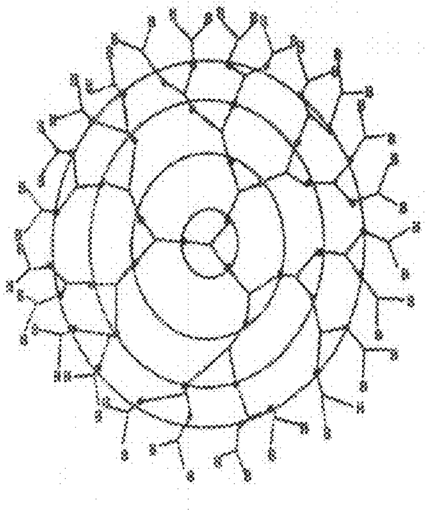
FIG. 2*a* shows by way of example a dendrimer, FIG. 2*b* a hyperbranched polymer.
Figure 2B:
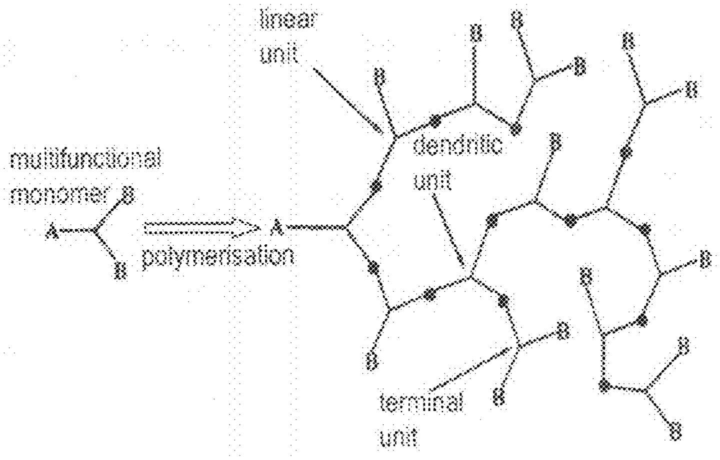
FIG. 2 shows diagrammatic examples of a dendritic carrier material.

The following abbreviations are used in the exemplary embodiments:

Boc tert-Butyloxycarbonyl
DIPEA Diisopropylethylamine
DMF Dimethylformamide
EDT Ethanedithiol
Fmoc 9-Fluorenylmethoxycarbonyl
HBTU 2-(1H-Benzotriazol-1-yl)-1,1,3,3-tetramethyl-uronium hexafluorophosphate
HPLC High-pressure liquid chromatography
Pmc 2,2,5,7,8-Pentamethylchromansulphonyl
tBu tert-Butyl
TES Triethylsilane
TFA Trifluoroacetic acid
Trt Triphenylmethyl

EXAMPLE 1

Production of a Peptide Signal Adjuvant

A nature-identical signal peptide with the sequence Tyr-Gly-Arg-Lys-Lys-Arg-Arg-Gln-Arg-Arg-Arg (Tat sequence) is produced by Fmoc/tBu strategy, with the alpha-aminofunction of the L-amino acids employed being Fmoc-protected, and the side chains of the trifunctional amino acids being protected by the following protective groups: Boc for lysine and tryptophan; tBu for aspartic acid, glutamic acid, serine, threonine and tyrosine; Pmc for arginine; Trt for cysteine, histidine, asparagine and glutamine.

The peptide is produced automatically in a Syroll peptide synthesizer (MultiSynTech, Witten, DE). For this purpose, in each case 70 mg of Fmoc-Gly-trityl-resin (loading 0.85 mmol/g; 59.5 μmol) are introduced into 5 ml plastic syringes with plastic frits. The side chain-protected Fmoc-amino acids are dissolved in 0.4 M DMF, and 0.4 M HBTU in DMF and 0.8 M DIPEA in DMF are employed as activating reagents, and the temporary Fmoc protective group is eliminated with 40% piperidine in DMF. Coupling of the amino acids, elimination of the Fmoc protective group and the washing steps takes place while stirring with a magnetic stirrer.

Synthesis protocol: the resin is first swollen with 2 ml of DMF for 5 min and filtered off with suction and then washed three times more with 2 ml of DMF. To eliminate the Fmoc protective group of the primary Fmoc-glycine, the resin is mixed with 1.2 ml of 40% piperidine/DMF for 15 min, filtered off with suction and again mixed with 1.2 ml of 40% piperidine/DMF for 15 min, filtered off with suction and washed four times with 2 ml of DMF. For the coupling, firstly 600 μl of the respective amino acid solution 0.4 M in DMF (240 μmol, 4 eq) and then 600 μl of 0.8 M DIPEA/DMF (480 μmol, 8 eq) and subsequently 600 μl of 0.4 M HBTU/DMF (240 μmol, 4 eq) are added to the resin. After 1 h, the coupling solution is filtered off with suction and the resin is washed four times with 2 ml of DMF. The further coupling cycles are carried out in analogy to the first position, with the Fmoc elimination taking place first as just described. A further Fmoc-protected amino acid is then coupled onto the washed activated product, and the resulting coupling product is again washed. After the last amino acid has been coupled, the Fmoc protective group is eliminated as indicated above, and the resin is then washed four times with 2 ml of DMF, 2 ml of methanol and 2 ml of dichloromethane and sucked dry. Subsequently, the resulting peptide is treated with 1.5 ml of TFA/EDT/TES/$H_2O$ (92.5:2.5:2.5:2.5) for 3 h in order to remove the side chain protective groups and to eliminate the assembled peptide from the solid support. After filtration of the resulting peptide, the peptide-containing filtrate is concentrated in an IR vacuum evaporator (TecConsult+Trading, Eggstätt, DE) to 0.5 ml in each case and, after addition of 3.5 ml of ice-cold diethyl ether, stored at −20° C. for 2 h. The precipitated peptide is then spun down and on three more occasions mixed with 3.5 ml of ice-cold diethyl ether, slurried, stored at −20° C. for 2 h and spun down again. The resulting peptide is then dried in vacuo. The resulting product was checked by HPLC and mass spectrometry.

The scavenger compounds required for the synthesis were purchased from Fluka (Seelze, DE). The synthesis resin originated from Rapp Polymere (Tübingen, DE), and the side chain-protective Fmoc-amino acids and HBTU originated from Novabiochem (Bad Soden, DE).

EXAMPLE 2

Production of a Particulate Formulation

For this purpose, a dendritic polymer (polyamidoamine (PAMAM) dendrimer) with a molar mass $M_w$ of 6909 g/mol, a melt viscosity at 80° C. of less than 3 Pa s, a degree of branching of 100% and a diameter of the PAMAM carrier molecule of about 36 Å at 100° C. is melted in a first mixing vessel.

Carboxyfluorescein (marker) is used to simulate an active ingredient. The carboxyfluorescein is metered together with the signal peptide produced in Example 1 into the first mixing vessel until a marker content of about 1% by weight and a signal peptide content of about 1% by weight based on the polymer melt is reached. The carboxyfluorescein and the signal peptide are dispersed in the polymer melt by vigorous mixing.

A mixture of 2% by weight pectin (stabilizer), 1% by weight lauryl ether sulphate (emulsifier) in 87% by weight water (solvent) are introduced into a second mixing vessel at 50° C. with stirring, into which 10% by weight polymer/marker/signal peptide dispersion is metered from the first mixing vessel while stirring continuously (the % by weight data are based here on the total weight of the emulsion in the second mixing vessel). After a residence time of up to 10 minutes, the resulting particulate formulations sediment. The resulting particles are then filtered off, washed with the volatile solvent ethanol and then dried in a vacuum, plate or tumble dryer.

Most of the resulting particles have a particle size of between 1 μm and 200 μm.

EXAMPLE 3

Proof of Barrier Transport of the Particulate Drug Delivery Systems

For this purpose, HeLa and CHO cells are incubated in 8-chamber cover slips (Nunc) in a Dulbecco's modified eagle's medium with and without pH indicators comprising 10 μM of the particulate drug delivery systems produced in Example 2 at 37° C. for 30 min. The cells are then washed with medium, detached by trypsinization for 5 min, suspended in PBS and immediately thereafter the average fluorescence intensity/cell is determined for a total of 10000 cells using a flow cytometer (BD FACSCalibur System, Becton Dickinson, Heidelberg, DE). Live cells are selected based on sideways and forwards scattering. The selected cells show an unimpaired morphology.

All measurements of active ingredient uptake are carried out with live cells with an inverse LSM510 laser canning microscope (Carl Zeiss, Göttingen, DE) using a Plan-Apochromat 63×1.4 N.A. objective. Incubation with peptide takes place as described for the flow cytometry. To detect the carboxyfluorescein, the fluorescence is excited with the 488 nm line of an argon ion laser through an HFT UV/488 beam divider; the fluorescence is detected with a BP 505-550 bandpass filter.

Figure 3:
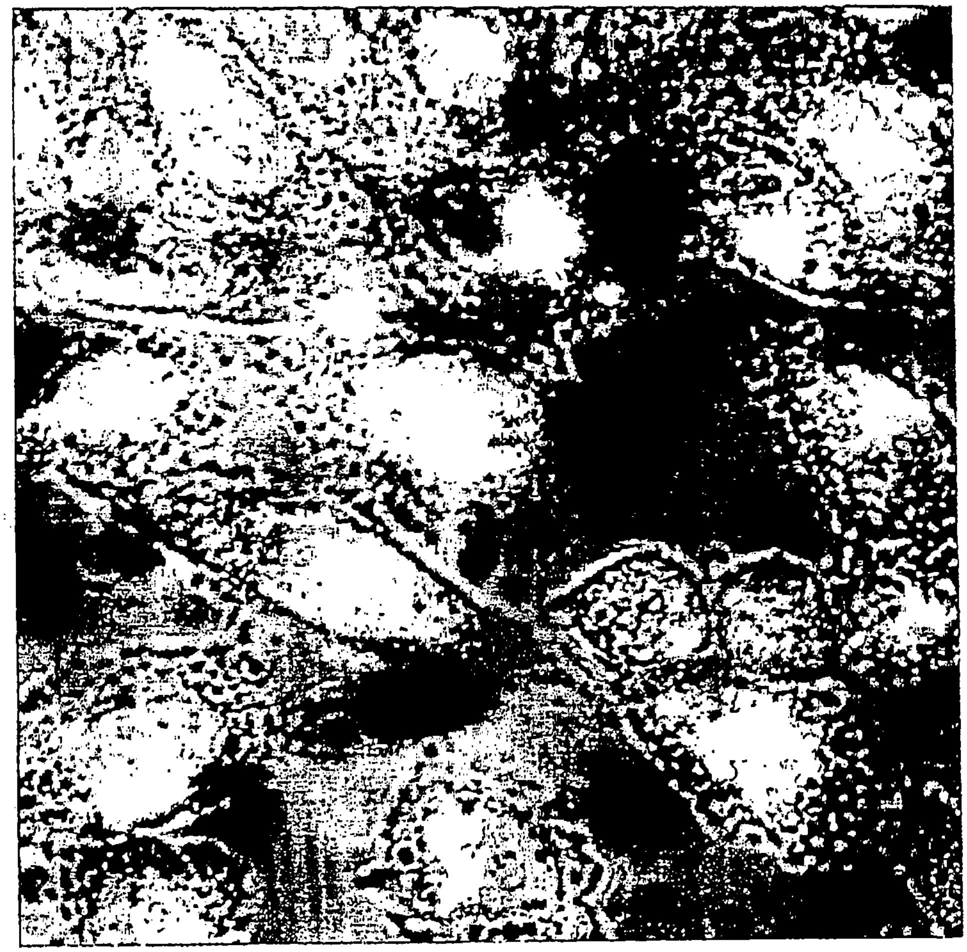
FIG. 3 shows a fluorescence micrograph of CHO cells which have been treated with drug delivery systems according to the invention, employing the Tat peptide as signal substance, and carboxyfluorescein (marker) as active ingredient analogue. The targeted uptake of the marker into the CHO cells is evident; fluorescence is virtually no longer evident outside the CHO cells after incubation for 30 minutes. This effect supports the idea that active ingredients can be transported through a cell membrane (barrier) with the described drug delivery system even by means of non-specifically bound extracellular stimuli ("hopping").

FIG. 3 shows by way of example the change in the signals from CHO cells after incubation for 30 minutes under the confocal fluorescence microscope. The good depth of penetration of the fluorescence signal ("active ingredient" signal) is evident. Accordingly, no covalent linkage of the signal peptide to the active ingredient or to the polymeric carrier is necessary in order to ensure transport of the active ingredient through the cell membrane.

In a further experiment, a particulate drug delivery system was produced in analogy to Examples 1 and 2 with a combination of the fluorescent dyes Cy3 (0.5% by weight) and Cy5 (0.5% by weight), and CHO cells were incubated therewith. Targeted uptake of both dyes into the CHO cells was detectable in this case too.

EXAMPLE 4

Human and Bovine Lactoferrin as Signal Substance

General:

Cells and reagents: The human HeLa carcinoma cells used are derived from the American Type Culture Collection (Manassas, Va., USA). HeLa cells were cultured in RPMI 1640 medium with stabilized glutamine and 2.0 g/l $NaHCO_3$ (PAN Biotech, Aidenbach, Germany) and with 10% foetal calf serum (PAN Biotech). Chlorbromazine was purchased from (Calbiochem (Bad Soden, Germany), 5-(N-ethyl-N-isopropyl)amiloride (EIPA), methyl-β-cyclodextrin (MβCD) and MTT [3-(4,5-dimethylthiazol-2-yl)-2,5-diphenyltetrazolium bromide] was purchased from Sigma (Deisenhofen, Germany).

Peptides: The peptides used were synthesized by EMC microcollections (Tübingen, Germany). The purity of all the peptides was checked by analytical HPLC. The identity of the peptides was confirmed by MALDI-TOF mass spectrometry. The purity of all the peptides was >95% (214 nm HPLC). The peptides were N-terminally labelled with carboxyfluorescein (as described in Fischer et al., Bioconjugate Chem. 14, 653-660, 2003).

Stock solution of the peptides: The peptides were taken up in DMSO to result in a 10 mM solution. The resulting stock solution was mixed further with PBS or medium. The peptide concentration of the DMSO stock solution was ascertained by means of the carboxyfluorescein absorption. This took place by UV/VIS spectrometry with a 1:100 dilution of the stock solution with 0.1M Tris/HCl buffer (pH 8.8), the absorption at 492 nm was measured, and carboxyfluorescein was assumed to have an extinction coefficient of 75000 l/(mol·cm).

Flow cytometry: To determine the efficiency of loading with peptides, HeLa cells were introduced at a density of 50000 per well in a 24-well plate (Sarstedt, Nümbrecht, Germany) into RPMI 1640-containing serum. After one day, the cells were washed with medium and dissolved with the peptides in the desired concentrations and incubated in 300 µl of RPMI 1640 for 30 min. Each mixture was carried out in triplicate. After the incubation, the cells were washed with medium and detached by trypsinization for 5 minutes, suspended in ice-cold PBS containing 0.1% (w/v) BSA and immediately determined by flow cytometry (BD FACS Calibur Systems, Becton Dickinson, Heidelberg, Germany). The fluorescence of 7000 vital cells was reached in each sample. Vital cells were identified by sideways and forwards scattering.

EXAMPLE 4.1

Efficiency of Uptake of Peptides of Human and Bovine Lactoferrin

The peptides derived from human or bovine lactoferrin were prepared by solid-phase peptide synthesis. To ascertain the uptake and the intracellular distribution of the peptides in live cells, both peptides were modified with carboxyfluorescein at the N terminus. In order to determine whether the derived lactoferrin peptides have an activity as cell-penetrating peptides, the cell-associated fluorescence of the HeLa cells incubated with bLF peptides or hLF peptides was determined by flow cytometry. For comparison, Antp and Tat peptides were selected as well-established cell-penetrating peptides.

Figure 4:
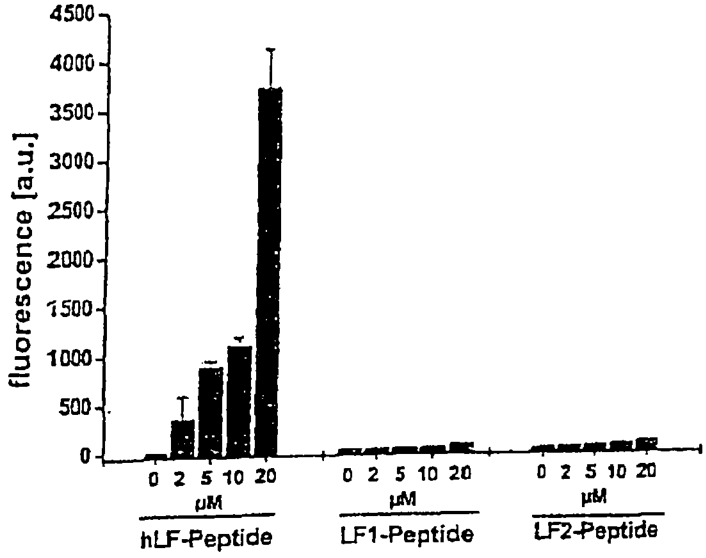
FIG. 4 shows the concentration dependence, measured by flow cytometry, of the uptake of various peptide signal substances into HeLa cells (Tat peptide, Antp peptide, hLF peptide (with an amino acid sequence according to positions 38 to 59 corresponding to SEQ ID No. 1), bLF peptide (with an amino acid sequence according to positions 33 to 50 corresponding to SEQ ID No. 2)).

As shown in FIG. 4, the cellular fluorescence, measured by flow cytometry, increases with increasing peptide concentration for all four peptides.

EXAMPLE 4.2

Determination of Structure-Activity Relationships

The hLF peptide, having 22 amino acids, is a medium-length cell-penetrating peptide. Nonaarginine has only nine amino acids, while the popular cell-penetrating peptide transportan has 27. Four of the seven cationic amino acids and the aromatic amino acid are in this case located near the cytosine residue. In the complete protein, the cytosine residue forms a disulphide bridge, whereby the domain forms a loop conformation. In addition, the cellular uptake of truncated peptides (LF1 and LF2, Table 1) lacking the terminal cysteine residue by comparison with the complete proteins was tested.

TABLE 1

Primary structure of the tested peptides

| No. | Peptide | Sequence |
|---|---|---|
| 1 | Tat peptide | Fluo-YGRKKRRQRRR-$CONH_2$ |
| 2 | Antp peptide | Fluo-RQIKIWFQNRRMKWKK-$CONH_2$ |
| 3 | hLF peptide | Fluo-KCFQWQRNMRKVRGPPVSCIKR-$CONH_2$ |
| 4 | bLF peptide | Fluo-PEWFKCRRWQWRMKKLGA-$CONH_2$ |
| 5 | LF1 peptide | Fluo-FQWQRNMRKVRGPPVS-$CONH_2$ |
| 6 | LF2 peptide | Fluo-FQWQRNMRKVR-$CONH_2$ |

All the peptides were synthesized as peptide amides. "Fluo" stands for 5(6)-carboxyfluorescein, and $CONH_2$ stands for the amidated C terminus of the peptides. The unmodified amino acid sequences correspond to SEQ ID No 3-6 (Table 1 entry No. 3-6), the unmodified Tat sequence corresponds to SEQ ID No. 27, and the unmodified Antp sequence corresponds to SEQ ID No. 28.

Figure 5:
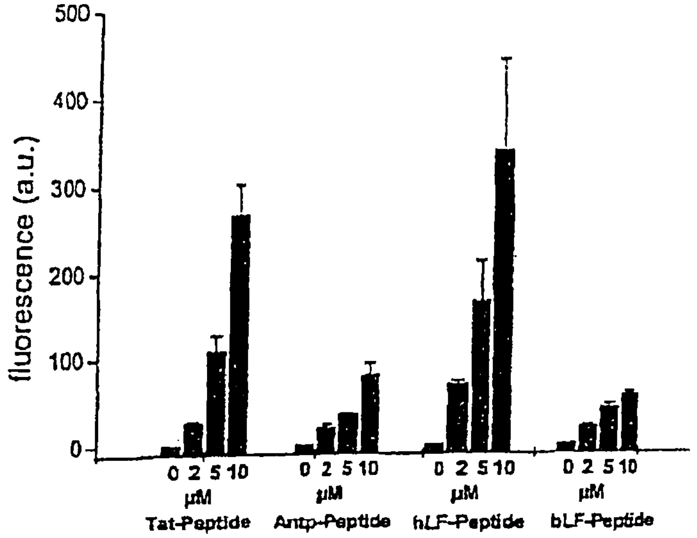
FIG. 5 shows the uptake, determined by flow cytometry, of fluorescein-labelled hLF peptides (with an amino acid sequence according to positions 38 to 59 corresponding to SEQ ID No. 1) compared with truncated peptides LF1 and LF2 (with an amino acid sequence according to positions 40 to 55 corresponding to SEQ ID No. 1 (LF1) and with an amino acid sequence according to positions 40 to 50 corresponding to SEQ ID No. 1 (LF2)).

The results of the flow cytometry are depicted in FIG. 5. The uptake of the peptides LF1 and LF2, lacking the cysteines, was only one-tenth of the amount taken up of hLF peptide which comprises both cysteine residues.

EXAMPLE 4.3

Cytotoxicity of hLF Peptides

Figure 6:
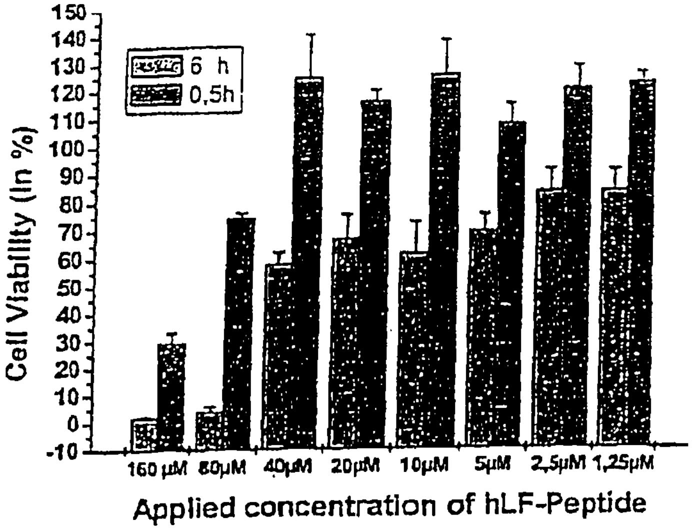
FIG. 6 shows the result of toxicity investigations on HeLa cells on incubation with various concentrations of hLF peptides (with an amino acid sequence according to positions 38 to 59 corresponding to SEQ ID No. 1) for 0.5 hour or 6 hours.
Figure 7A:
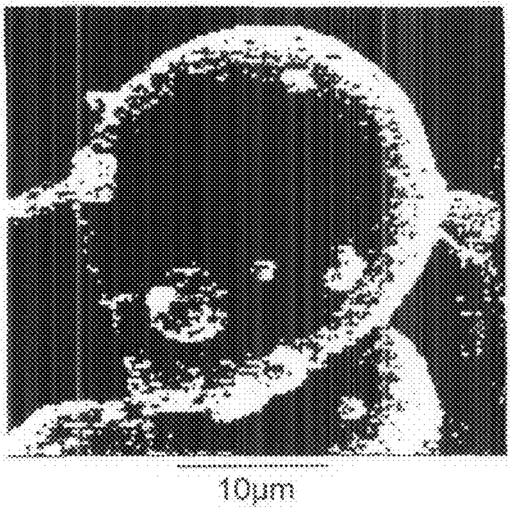
FIG. 7 shows particulate drug delivery systems which comprise α-lipoic acid (FIGS. 7 A and B) or a signal peptide derived from human lactoferrin and α-lipoic acid (FIGS. 7 C and D).
Figure 7B:
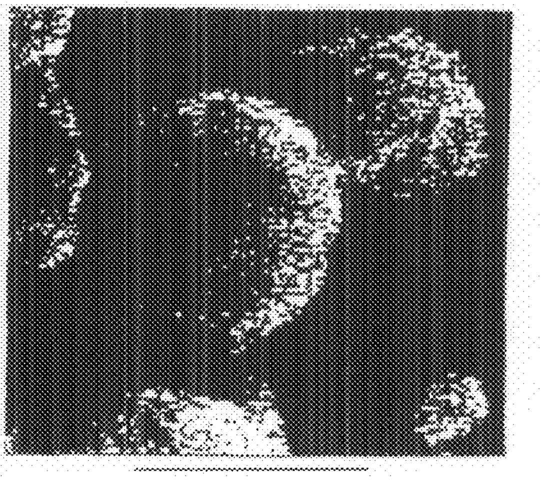
Figure 7C:
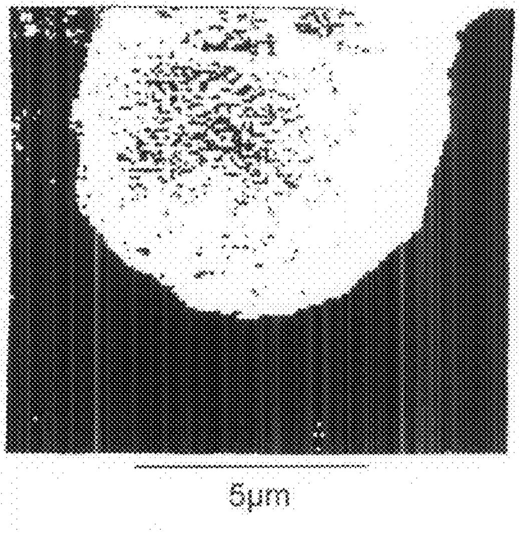
Figure 7D:
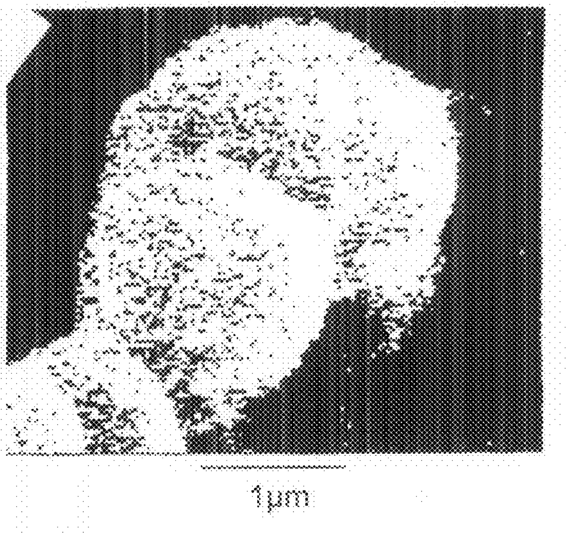

In the experiments described above, hLF peptide concentrations of around 40 µM were employed, whereby no cytotoxic effects were observed. However, relatively short incubation times of less than one hour were used when observing peptide uptake in live cells. In addition, therefore, the effect of longer incubation times and higher concentrations of the peptides on the ability of the cells to survive was tested. HeLa cells were for this purpose incubated with hLF peptide at a concentration of 1.25 µM to 160 µm for 0.5 or 6 h. The vitality of the cells was then determined with an MTT test. The results are summarized in FIG. 6.

No cytotoxic effects could be observed in cells incubated for only 30 min with the peptide up to a concentration of 40 µM. The ability of the cells to survive was slightly reduced at a peptide concentration of 5 µM after 6 h. The cells were killed at concentrations above 40 µM.

EXAMPLE 5

Loading of Drug Delivery Particles with and Without Human Lactoferrin-Derived Signal Peptides and α-Lipoic Acid

EXAMPLE 5.1

The hyperbranched polyester employed was obtained by hydrophobicizing a hydrophilic hyper-branched polyester (commercially available from Perstorp® under the name Boltorn H30®) which had a weight average molecular weight $M_w$ of 3500 g/mol, a glass transition temperature of about 35° C. and a hydroxy number of about 490 mg KOH/g. The hydrophobicizing took place by esterifying the hydrophilic polymer with a mixture of stearic acid and palmitic acid (ratio of stearic acid to palmitic acid=2 to 1 based on mass), with 50% of the hydroxy groups of the hydrophilic polymer being reacted. The molecular weight $M_w$ was 7500 g/mol.

The product was produced by dissolving 20% by weight of α-lipoic acid (CAS: 62-46-4; commercially available from Degussa® AG) in the molten polymer at a temperature of about 65° C. with a spiral stirrer (200 rpm) in a first mixing vessel within 5 minutes.

A mixture of surfactants consisting of 1% by weight polyvinyl alcohol (M=6000 g/mol, Polisciences®, Warrington, USA) and 0.1% by weight of an ethoxylated fatty alcohol (Tego® Alkanol L4 from Degussa® AG) was introduced into water at 50° C. with stirring in a further mixing vessel.

Subsequently, the polymer melt prepared in the first mixing vessel and containing besides the polymer also the substance to be encapsulated was transferred from the first mixing vessel while stirring continuously (ULTRA-TURRAX, 3000 rpm) into the second mixing vessel at 50° C.

Particles formed after a residence time of 2 minutes and cooling of the composition contained in the second mixing vessel to a temperature which was 25° C. below the melting point of the polymer. The suspension was passed through a tubing pump to a centrifuge in which the active ingredient particles were separated from the continuous phase at 25° C. The active ingredient particles were then dried at 25° C. and 10 mbar in a vacuum dryer for 100 h.

The particles were free of unwanted solvents and consisted of the hyperbranched fatty acid-modified polyester and about 4% by weight of α-lipoic acid, based on the mass of particles.

The α-lipoic acid particle content was determined by HPLC after extraction with methanol or methanol/water, and 5.4% by weight of α-lipoic acid (thioctic acid) were present.

A sample of the particles obtained in this way was swollen with the signal peptide of Example 4, Table 1, No. 3 in an acetonitrile/water solution for about 30 min and filtered off with suction on a filter, and the externally dry fluorescent polymer material was then fixed on a tantalum support a paper filter strip with the loaded polymer material by means of adhesive tape and dried under high vacuum overnight in order to remove traces of acetonitrile.

Part of the samples were dried and fixed and contacted on a graphite adhesive sheet. The morphology on the sample material was visualized by scanning electron micrographs. The corresponding scans are depicted in FIG. 7. FIGS. 7 A and 7 B show electron micrographs of particles loaded with α-lipoic acid. FIGS. 7 C and 7 D show electron micrographs of particles loaded with α-lipoic acid and the signal peptide.
Scanning Conditions:
Microscope: Jeol JSM 6400
Acceleration voltage: 20 KV
Operating distance: 15 mm The resulting particles (with and without signal peptide loading) were characterized by surface-analytical X-ray photon electron spectroscopy (XPS) (XPS surface analyser from Leybold, Cologne, Mg edge). The results are represented in Tables 2 and 3. The particles without peptides showed the atom-specific signals of the carrier polymer (C and O), and the formulation with signal peptide additionally showed the characteristic nitrogen (N) signal. The result shows that carrier, signal peptide and active ingredient are in the form of a simple aggregation, that is not covalently linked. The signal peptide is additionally detectable on the particle surface.

TABLE 2

| Element | Atom % | Orbit | Reg | Range |
|---------|--------|-------|-----|-------|
| C | 90.30 | 1s | | 291.8 . . . 279.6 |
| O | 9.10 | 1s | a2 | 533.6 . . . 528.7 |
| S | 0.60 | 2p | a5 | 167.2 . . . 161 |

TABLE 3

| Element | Atom % | Orbit | Reg | Range |
|---------|--------|-------|-----|-------|
| C | 91.17 | 1s | | 291.6 . . . 280.3 |
| N | 0.22 | 1s | a3 | 402.2 . . . 398.3 |
| O | 8.34 | 1s | a2 | 534 . . . 528.3 |
| S | 0.27 | 2p | a5 | 166 . . . 162.2 |

EXAMPLE 5.2

The product was produced by dissolving 1% by weight α-lipoic acid (CAS: 62-46-4; commercially available from Degussa® AG) and 4% by weight poly(DL-lactide-co-glycolide) (CAS: 26780-50-7, commercially available as RESOMER® RG 502H from Boehringer Ingelheim) in 95% by volume acetonitrile at room temperature using a paddle stirrer (200 rpm) in a first mixing vessel within 5 minutes.

1% by weight of an ethoxylated fatty alcohol (Tego® Alkanol L4 from Degussa® AG) in rapeseed oil (EAN No. 22112682, obtainable from Associated Oil Packers GmbH) was introduced with stirring at room temperature into a further mixing vessel.

Then the polymer solution which was prepared in the first mixing vessel and which, besides the polymer, also comprised the substance being encapsulated was transferred from the first mixing vessel while stirring continuously (propeller stirrer, 500 rpm) into a second mixing vessel at room temperature.

After a residence time of 3 hours, the organic solvent was evaporated and particles formed. The vegetable oil was mixed with n-hexane (in the ratio 1:1 by mass) in the same mixing vessel and then the particles were filtered off. The filtered particles were dried in a vacuum dryer at 50° C. and 10 mbar for 100 h.

The α-lipoic acid particle content was determined by HPLC after extraction with methanol or methanol/water, and 0.4% by weight of α-lipoic acid (thioctic acid) was present.

The invention claimed is:

1. A particulate drug delivery system, comprising:

a polymeric carrier, at least one signal substance for transport through a biological barrier comprising at least one peptide derived from a lactoferrin protein which consists of SEQ ID No. 3, SEQ ID No. 4, SEQ ID No. 29, or SEQ ID No. 30, and at least one active ingredient, wherein the polymeric carrier, signal substance and active ingredient have no covalent linkages with one another.

2. The particulate drug delivery system of claim 1, wherein both the signal substance and the active ingredient are present dispersed or coacervated in the polymeric carrier.

3. The particulate drug delivery system of claim 1, wherein the polymeric carrier comprises at least one branched or crosslinked polymer with a proportion of more than 50% by weight based on the total weight of the carrier.

4. The particulate drug delivery system of claim 1, wherein the polymeric carrier is a dendritic polymer.

5. The particulate drug delivery system of claim 1, wherein the polymeric carrier is a branched hydrogel or a comb polymer.

6. The particulate drug delivery system of claim 1, wherein the polymeric carrier is a dendritic polymer having a molar mass above 1000 g/mol and/or a melt viscosity of less than 3.0 Pas at 80° C.

7. The particulate drug delivery system of claim 1, wherein the polymeric carrier is at least one of a dendritic polymer selected from the group consisting of polyamidoamine dendrimers, of polypropyleneimine dendrimers, of polyethylene oxide-based dendrimers, of polyether dendrimers, of polyamido dendrimers, of polylysine dendrimers, of polyaryl ether dendrimers, a dendritic polymer selected from the group consisting of polyesters, polyesteramides, polyethers, polyamides, polyethyleneimines; polycaprolactones, polyglycerols, polyglycolides, polylactides, polylactide-co-glycolides, polytartrates and polysaccharides, or a branched or crosslinked carrier polymer selected from the group consisting of natural and artificial carbohydrate homo- or copolymers, of natural and artificial amino acid polymers, of natural and artificial nucleic acids, of polyamines, of polyimines, of polyesters, of polyethers, of polyols, of polyolefins, of polyalkylene glycols, of polyamides, of polyacetals, of polyacrylates, of polyacetates, of polyurethanes, of organosilicon polymers, of epoxy resins, of polythiols, of polycarbonates, of polycaprolactones, of polyglycolides, of polylactides, of polylactide-co-glycolides and of polytartrates.

8. The particulate drug delivery system of claim 1, wherein the active ingredient is an unmodified active pharmaceutical ingredient.

9. The particulate drug delivery system of claim 1, wherein the active ingredient and/or signal substance are non-specifically aggregated in different layers in the drug delivery particles.

10. The particulate drug delivery system of claim 1, wherein there is non-specific aggregation of the active ingredient in an inner layer and of the signal substance in a subsequent layer in the particulate drug delivery system.

11. The particulate drug delivery system of claim 1, which comprises at least one active ingredient selected from the group consisting of antibodies, peptide hormones, receptors or peptidic ligands thereof, enzymes, interferons, tumor necrosis factor, cachectin, dihydrofolate reductase, lymphotoxin, interleukins, tumor suppressor proteins, plasmin, urokinase, hirudin, streptokinase, urokinase, tissue plasminogen activator, protein C, protein S, phospholipase $A_2$, uromodulin, Tamm-Horsfall protein, insulin, trypsin inhibitor, lysozyme, thymopoietin, peptide antibiotics, erythropoietin, hepatotherapeutic substances, neuroprotective substances, immunotherapeutics, immunosuppressants, low molecular weight active ingredients for cardiovascular disorders or cancer, analgesics, low molecular weight antiinflammatory, antibiotic antimicrobial active ingredients, low molecular weight hormones, nucleic acid fragments, nucleic acids, nucleoside analogs, β-interferons, α-lipoic acid, peptide analogs, enzyme or receptor inhibitors, enzyme or receptor agonists, enzyme or receptor antagonists, prostaglandins, steroids, cytostatics, heterocyclic antibiotics and prodrugs thereof.

12. The particulate drug delivery system of claim 1, wherein the active ingredient is α-lipoic acid.

13. The particulate drug delivery system of claim 1, wherein the polymeric carrier is a polylactide-co-glycolide.

14. The particulate drug delivery system of claim 1, wherein the signal substance consists of SEQ ID NO:3.

15. The particulate drug delivery system of claim 1, wherein the signal substance consists of SEQ ID NO:4.

16. The particulate drug delivery system of claim 1, wherein the signal substance consists of SEQ ID NO:29.

17. The particulate drug delivery system of claim 1, wherein the signal substance consists of SEQ ID NO:30.

18. A method of producing the particulate drug delivery system of claim 1, comprising combining the polymeric carrier, signal substance and active ingredient into a particulate form.

* * * * *

SEQUENCE LISTING

<160> NUMBER OF SEQ ID NOS: 35

<210> SEQ ID NO 1
<211> LENGTH: 711
<212> TYPE: PRT
<213> ORGANISM: Homo sapiens -continued

<400> SEQUENCE: 1

```
Met Lys Leu Val Phe Leu Val Leu Leu Phe Leu Gly Ala Leu Gly Leu
1               5                   10                  15

Cys Leu Ala Gly Arg Arg Arg Arg Ser Val Gln Trp Cys Ala Val Ser
            20                  25                  30

Gln Pro Glu Ala Thr Lys Cys Phe Gln Trp Gln Arg Asn Met Arg Lys
        35                  40                  45

Val Arg Gly Pro Pro Val Ser Cys Ile Lys Arg Asp Ser Pro Ile Gln
    50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
        115                 120                 125

Leu Gln Gly Leu Lys Ser Cys His Thr Gly Leu Arg Arg Thr Ala Gly
    130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
            180                 185                 190

Cys Ala Gly Thr Gly Glu Asn Lys Cys Ala Phe Ser Ser Gln Glu Pro
        195                 200                 205

Tyr Phe Ser Tyr Ser Gly Ala Phe Lys Cys Leu Arg Asp Gly Ala Gly
    210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Lys Pro Val Asp Lys Phe Lys Asp Cys His Leu Ala Arg Val Pro Ser
            260                 265                 270

His Ala Val Val Ala Arg Ser Val Asn Gly Lys Glu Asp Ala Ile Trp
        275                 280                 285

Asn Leu Leu Arg Gln Ala Gln Glu Lys Phe Gly Lys Asp Lys Ser Pro
    290                 295                 300

Lys Phe Gln Leu Phe Gly Ser Pro Ser Gly Gln Lys Asp Leu Leu Phe
305                 310                 315                 320

Lys Asp Ser Ala Ile Gly Phe Ser Arg Val Pro Pro Arg Ile Asp Ser
                325                 330                 335

Gly Leu Tyr Leu Gly Ser Gly Tyr Phe Thr Ala Ile Gln Asn Leu Arg
            340                 345                 350

Lys Ser Glu Glu Glu Val Ala Ala Arg Arg Ala Arg Val Val Trp Cys
        355                 360                 365

Ala Val Gly Glu Gln Glu Leu Arg Lys Cys Asn Gln Trp Ser Gly Leu
    370                 375                 380

Ser Glu Gly Ser Val Thr Cys Ser Ser Ala Ser Thr Thr Glu Asp Cys
385                 390                 395                 400

Ile Ala Leu Val Leu Lys Gly Glu Ala Asp Ala Met Ser Leu Asp Gly
```

-continued

```
                405                 410                 415

Gly Tyr Val Tyr Thr Ala Gly Lys Cys Gly Leu Val Pro Val Leu Ala
            420                 425                 430

Glu Asn Tyr Lys Ser Gln Gln Ser Ser Asp Pro Asp Pro Asn Cys Val
        435                 440                 445

Asp Arg Pro Val Glu Gly Tyr Leu Ala Val Ala Val Val Arg Arg Ser
    450                 455                 460

Asp Thr Ser Leu Thr Trp Asn Ser Val Lys Gly Lys Lys Ser Cys His
465                 470                 475                 480

Thr Ala Val Asp Arg Thr Ala Gly Trp Asn Ile Pro Met Gly Leu Leu
                485                 490                 495

Phe Asn Gln Thr Gly Ser Cys Lys Phe Asp Glu Tyr Phe Ser Gln Ser
            500                 505                 510

Cys Ala Pro Gly Ser Asp Pro Arg Ser Asn Leu Cys Ala Leu Cys Ile
        515                 520                 525

Gly Asp Glu Gln Gly Glu Asn Lys Cys Val Pro Asn Ser Asn Glu Arg
    530                 535                 540

Tyr Tyr Gly Tyr Thr Gly Ala Phe Arg Cys Leu Ala Glu Asn Ala Gly
545                 550                 555                 560

Asp Val Ala Phe Val Lys Asp Val Thr Val Leu Gln Asn Thr Asp Gly
                565                 570                 575

Asn Asn Asn Glu Ala Trp Ala Lys Asp Leu Lys Leu Ala Asp Phe Ala
            580                 585                 590

Leu Leu Cys Leu Asp Gly Lys Arg Lys Pro Val Thr Glu Ala Arg Ser
        595                 600                 605

Cys His Leu Ala Met Ala Pro Asn His Ala Val Val Ser Arg Met Asp
    610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
                645                 650                 655

Glu Thr Lys Asn Leu Leu Phe Asn Asp Asn Thr Glu Cys Leu Ala Arg
            660                 665                 670

Leu His Gly Lys Thr Thr Tyr Glu Lys Tyr Leu Gly Pro Gln Tyr Val
        675                 680                 685

Ala Gly Ile Thr Asn Leu Lys Lys Cys Ser Thr Ser Pro Leu Leu Glu
    690                 695                 700

Ala Cys Glu Phe Leu Arg Lys
705                 710


<210> SEQ ID NO 2
<211> LENGTH: 708
<212> TYPE: PRT
<213> ORGANISM: Homo sapiens

<400> SEQUENCE: 2

Met Lys Leu Phe Val Pro Ala Leu Leu Ser Leu Gly Ala Leu Gly Leu
1               5                   10                  15

Cys Leu Ala Ala Pro Arg Lys Asn Val Arg Trp Cys Thr Ile Ser Gln
            20                  25                  30

Pro Glu Trp Phe Lys Cys Arg Arg Trp Gln Trp Arg Met Lys Lys Leu
        35                  40                  45

Gly Ala Pro Ser Ile Thr Cys Val Arg Arg Ala Phe Ala Leu Glu Cys
    50                  55                  60
```

-continued

```
Ile Arg Ala Ile Ala Glu Lys Lys Ala Asp Ala Val Thr Leu Asp Gly
65                  70                  75                  80

Gly Met Val Phe Glu Ala Gly Arg Asp Pro Tyr Lys Leu Arg Pro Val
                85                  90                  95

Ala Ala Glu Ile Tyr Gly Thr Lys Glu Ser Pro Gln Thr His Tyr Tyr
            100                 105                 110

Ala Val Ala Val Val Lys Lys Gly Ser Asn Phe Gln Leu Asp Gln Leu
        115                 120                 125

Gln Gly Arg Lys Ser Cys His Thr Gly Leu Gly Arg Ser Ala Gly Trp
    130                 135                 140

Ile Ile Pro Met Gly Ile Leu Arg Pro Tyr Leu Ser Trp Thr Glu Ser
145                 150                 155                 160

Leu Glu Pro Leu Gln Gly Ala Val Ala Lys Phe Phe Ser Ala Ser Cys
                165                 170                 175

Val Pro Cys Ile Asp Arg Gln Ala Tyr Pro Asn Leu Cys Gln Leu Cys
            180                 185                 190

Lys Gly Glu Gly Glu Asn Gln Cys Ala Cys Ser Ser Arg Glu Pro Tyr
        195                 200                 205

Phe Gly Tyr Ser Gly Ala Phe Lys Cys Leu Gln Asp Gly Ala Gly Asp
    210                 215                 220

Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Ser Arg Ala
                245                 250                 255

Pro Val Asp Ala Phe Lys Glu Cys His Leu Ala Gln Val Pro Ser His
            260                 265                 270

Ala Val Val Ala Arg Ser Val Asp Gly Lys Glu Asp Leu Ile Trp Lys
        275                 280                 285

Leu Leu Ser Lys Ala Gln Glu Lys Phe Gly Lys Asn Lys Ser Arg Ser
    290                 295                 300

Phe Gln Leu Phe Gly Ser Pro Pro Gly Gln Arg Asp Leu Leu Phe Lys
305                 310                 315                 320

Asp Ser Ala Leu Gly Phe Leu Arg Ile Pro Ser Lys Val Asp Ser Ala
                325                 330                 335

Leu Tyr Leu Gly Ser Arg Tyr Leu Thr Thr Leu Lys Asn Leu Arg Glu
            340                 345                 350

Thr Ala Glu Glu Val Lys Ala Arg Tyr Thr Arg Val Val Trp Cys Ala
        355                 360                 365

Val Gly Pro Glu Glu Gln Lys Lys Cys Gln Gln Trp Ser Gln Gln Ser
    370                 375                 380

Gly Gln Asn Val Thr Cys Ala Thr Ala Ser Thr Thr Asp Asp Cys Ile
385                 390                 395                 400

Val Leu Val Leu Lys Gly Glu Ala Asp Ala Leu Asn Leu Asp Gly Gly
                405                 410                 415

Tyr Ile Tyr Thr Ala Gly Lys Cys Gly Leu Val Pro Val Leu Ala Glu
            420                 425                 430

Asn Arg Lys Ser Ser Lys His Ser Ser Leu Asp Cys Val Leu Arg Pro
        435                 440                 445

Thr Glu Gly Tyr Leu Ala Val Ala Val Val Lys Lys Ala Asn Glu Gly
    450                 455                 460

Leu Thr Trp Asn Ser Leu Lys Asp Lys Lys Ser Cys His Thr Ala Val
465                 470                 475                 480

Asp Arg Thr Ala Gly Trp Asn Ile Pro Met Gly Leu Ile Val Asn Gln
```

-continued

```
            485                 490                 495

Thr Gly Ser Cys Ala Phe Asp Glu Phe Phe Ser Gln Ser Cys Ala Pro
            500                 505                 510

Gly Ala Asp Pro Lys Ser Arg Leu Cys Ala Leu Cys Ala Gly Asp Asp
        515                 520                 525

Gln Gly Leu Asp Lys Cys Val Pro Asn Ser Lys Glu Lys Tyr Tyr Gly
    530                 535                 540

Tyr Thr Gly Ala Phe Arg Cys Leu Ala Glu Asp Val Gly Asp Val Ala
545                 550                 555                 560

Phe Val Lys Asn Asp Thr Val Trp Glu Asn Thr Asn Gly Glu Ser Thr
                565                 570                 575

Ala Asp Trp Ala Lys Asn Leu Asn Arg Glu Asp Phe Arg Leu Leu Cys
            580                 585                 590

Leu Asp Gly Thr Arg Lys Pro Val Thr Glu Ala Gln Ser Cys His Leu
        595                 600                 605

Ala Val Ala Pro Asn His Ala Val Val Ser Arg Ser Asp Arg Ala Ala
    610                 615                 620

His Val Lys Gln Val Leu Leu His Gln Gln Ala Leu Phe Gly Lys Asn
625                 630                 635                 640

Gly Lys Asn Cys Pro Asp Lys Phe Cys Leu Phe Lys Ser Glu Thr Lys
                645                 650                 655

Asn Leu Leu Phe Asn Asp Asn Thr Glu Cys Leu Ala Lys Leu Gly Gly
            660                 665                 670

Arg Pro Thr Tyr Glu Glu Tyr Leu Gly Thr Glu Tyr Val Thr Ala Ile
        675                 680                 685

Ala Asn Leu Lys Lys Cys Ser Thr Ser Pro Leu Leu Glu Ala Cys Ala
    690                 695                 700

Phe Leu Thr Arg
705


<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Cys Phe Gln Trp Gln Arg Asn Met Arg Lys Val Arg Gly Pro Pro
1               5                   10                  15

Val Ser Cys Ile Lys Arg
            20


<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Phe Gln Trp Gln Arg Asn Met Arg Lys Val Arg Gly Pro Pro Val
1               5                   10                  15

Ser Cys


<210> SEQ ID NO 5
```

-continued

<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 5

```
Phe Gln Trp Gln Arg Asn Met Arg Lys Val Arg Gly Pro Pro Val Ser
1               5                   10                  15
```

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 6

```
Phe Gln Trp Gln Arg Asn Met Arg Lys Val Arg
1               5                   10
```

<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 7

```
Lys Cys Phe Gln Trp Gln Arg Asn Val Arg Lys Val Arg Gly Pro Pro
1               5                   10                  15

Val Ser Cys Ile Lys Arg
            20
```

<210> SEQ ID NO 8
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 8

```
Lys Cys Phe Gln Trp Gln Arg Asn Ile Arg Lys Val Arg Gly Pro Pro
1               5                   10                  15

Val Ser Cys Ile Lys Arg
            20
```

<210> SEQ ID NO 9
<211> LENGTH: 22
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (9)..(9)
<223> OTHER INFORMATION: norvaline

<400> SEQUENCE: 9

```
Lys Cys Phe Gln Trp Gln Arg Asn Xaa Arg Lys Val Arg Gly Pro Pro
1               5                   10                  15

Val Ser Cys Ile Lys Arg
```

-continued

20

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Lys Cys Phe Gln Trp Gln Arg Asn Leu Arg Lys Val Arg Gly Pro Pro
1 5 10 15

Val Ser Cys Ile Lys Arg
20

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Cys Phe Gln Trp Gln Arg Asn Val Arg Lys Val Arg Gly Pro Pro Val
1 5 10 15

Ser Cys

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Cys Phe Gln Trp Gln Arg Asn Ile Arg Lys Val Arg Gly Pro Pro Val
1 5 10 15

Ser Cys

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (8)..(8)
<223> OTHER INFORMATION: norvaline

<400> SEQUENCE: 13

Cys Phe Gln Trp Gln Arg Asn Xaa Arg Lys Val Arg Gly Pro Pro Val
1 5 10 15

Ser Cys

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Cys Phe Gln Trp Gln Arg Asn Leu Arg Lys Val Arg Gly Pro Pro Val
1 5 10 15

Ser Cys

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (8)..(8)
<223> OTHER INFORMATION: norleucine

<400> SEQUENCE: 15

Cys Phe Gln Trp Gln Arg Asn Xaa Arg Lys Val Arg Gly Pro Pro Val
1 5 10 15

Ser Cys

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Phe Gln Trp Gln Arg Asn Val Arg Lys Val Arg Gly Pro Pro Val Ser
1 5 10 15

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Phe Gln Trp Gln Arg Asn Ile Arg Lys Val Arg Gly Pro Pro Val Ser
1 5 10 15

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (7)..(7)
<223> OTHER INFORMATION: norvaline

<400> SEQUENCE: 18

Phe Gln Trp Gln Arg Asn Xaa Arg Lys Val Arg Gly Pro Pro Val Ser
1 5 10 15

<210> SEQ ID NO 19
<211> LENGTH: 16
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 19

Phe Gln Trp Gln Arg Asn Leu Arg Lys Val Arg Gly Pro Pro Val Ser
1               5                   10                  15


<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: norleucine

<400> SEQUENCE: 20

Phe Gln Trp Gln Arg Asn Xaa Arg Lys Val Arg Gly Pro Pro Val Ser
1               5                   10                  15


<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Phe Gln Trp Gln Arg Asn Val Arg Lys Val Arg
1               5                   10


<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Phe Gln Trp Gln Arg Asn Ile Arg Lys Val Arg
1               5                   10


<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: norvaline

<400> SEQUENCE: 23

Phe Gln Trp Gln Arg Asn Xaa Arg Lys Val Arg
1               5                   10


<210> SEQ ID NO 24
<211> LENGTH: 11
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 24

Phe Gln Trp Gln Arg Asn Leu Arg Lys Val Arg
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: norleucine

<400> SEQUENCE: 25

Phe Gln Trp Gln Arg Asn Xaa Arg Lys Val Arg
1               5                   10

<210> SEQ ID NO 26
<211> LENGTH: 66
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
aaatgcttcc aatggcaaag gaatatgaga aaagtgcgtg gccctcctgt cagctgcata     60
aagaga                                                                66

<210> SEQ ID NO 27
<211> LENGTH: 2136
<212> TYPE: DNA
<213> ORGANISM: Homo sapiens

<400> SEQUENCE: 27
atgaaacttg tcttcctcgt cctgctgttc ctcggggccc tcggactgtg tctggctggc     60
cgtaggagaa ggagtgttca gtggtgcgcc gtatcccaac ccgaggccac aaaatgcttc    120
caatggcaaa ggaatatgag aaaagtgcgt ggccctcctg tcagctgcat aaagagagac    180
tcccccatcc agtgtatcca ggccattgcg gaaaacaggg ccgatgctgt gacccttgat    240
ggtggtttca tatacgaggc aggcctggcc ccctacaaac tgcgacctgt agcggcggaa    300
gtctacggga ccgaaagaca gccacgaact cactattatg ccgtggctgt ggtgaagaag    360
ggcggcagct ttcagctgaa cgaactgcaa ggtctgaagt cctgccacac aggccttcgc    420
aggaccgctg gatggaatgt ccctacaggg acacttcgtc cattcttgaa ttggacgggt    480
ccacctgagc ccattgaggc agctgtggcc aggttcttct cagccagctg tgttcccggt    540
gcagataaag gacagttccc caacctgtgt cgcctgtgtg cggggacagg ggaaaacaaa    600
tgtgccttct cctcccagga accgtacttc agctactctg gtgccttcaa gtgtctgaga    660
gacggggctg gagacgtggc ttttatcaga gagagcacag tgtttgagga cctgtcagac    720
gaggctgaaa gggacgagta tgagttactc tgcccagaca acactcggaa gccagtggac    780
aagttcaaag actgccatct ggcccgggtc ccttctcatg ccgttgtggc acgaagtgtg    840
aatggcaagg aggatgccat ctggaatctt ctccgccagg cacaggaaaa gtttggaaag    900

-continued

```
gacaagtcac cgaaattcca gctctttggc tcccctagtg ggcagaaaga tctgctgttc    960

aaggactctg ccattgggtt ttcgagggtg cccccgagga tagattctgg gctgtacctt   1020

ggctccggct acttcactgc catccagaac ttgaggaaaa gtgaggagga agtggctgcc   1080

cggcgtgcgc gggtcgtgtg gtgtgcggtg ggcgagcagg agctgcgcaa gtgtaaccag   1140

tggagtggct tgagcgaagg cagcgtgacc tgctcctcgg cctccaccac agaggactgc   1200

atcgccctgg tgctgaaagg agaagctgat gccatgagtt tggatggagg atatgtgtac   1260

actgcatgca aatgtggttt ggtgcctgtc ctggcagaga actacaaatc ccaacaaagc   1320

agtgaccctg atcctaactg tgtggataga cctgtggaag gatatcttgc tgtggcggtg   1380

gttaggagat cagacactag ccttacctgg aactctgtga aaggcaagaa gtcctgccac   1440

accgccgtgg acaggactgc aggctggaat atccccatgg gcctgctctt caaccagacg   1500

ggctcctgca aatttgatga atatttcagt caaagctgtg cccctgggtc tgacccgaga   1560

tctaatctct gtgctctgtg tattggcgac gagcagggtg agaataagtg cgtgcccaac   1620

agcaacgaga gatactacgg ctacactggg gctttccggt gcctggctga gaatgctgga   1680

gacgttgcat ttgtgaaaga tgtcactgtc ttgcagaaca ctgatggaaa taacaatgag   1740

gcatgggcta aggatttgaa gctggcagac tttgcgctgc tgtgcctcga tggcaaacgg   1800

aagcctgtga ctgaggctag aagctgccat cttgccatgg ccccgaatca tgccgtggtg   1860

tctcggatgg ataaggtgga acgcctgaaa caggtgctgc tccaccaaca ggctaaattt   1920

gggagaaatg gatctgactg cccggacaag ttttgcttat tccagtctga aaccaaaaac   1980

cttctgttca atgacaacac tgagtgtctg gccagactcc atggcaaaac aacatatgaa   2040

aaatatttgg gaccacagta tgtcgcaggc attactaatc tgaaaaagtg ctcaacctcc   2100

cccctcctgg aagcctgtga attcctcagg aagtaa                             2136
```

<210> SEQ ID NO 28
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: norleucine

<400> SEQUENCE: 28

```
Lys Cys Phe Gln Trp Gln Arg Asn Xaa Arg Lys Val Arg Gly Pro Pro
1               5                   10                  15

Val Ser Cys Ile Lys Arg
            20
```

<210> SEQ ID NO 29
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Lys Cys Arg Arg Trp Gln Trp Arg Met Lys Lys Leu Gly Ala Pro Ser
1               5                   10                  15

Ile Thr Cys Val Arg Arg
            20
```

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Cys Arg Arg Trp Gln Trp Arg Met Lys Lys Leu Gly Ala Pro Ser Ile
1 5 10 15

Thr Cys

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Arg Gln Ile Lys Ile Trp Phe Gln Asn Arg Arg Met Lys Trp Lys Lys
1 5 10 15

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Arg Arg Arg Arg Arg Arg Arg Arg Arg
1 5

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Tyr Gly Arg Lys Lys Arg Arg Gln Arg Arg Arg
1 5 10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Tyr Gly Arg Lys Lys Arg Arg Gln Arg Arg Arg
1 5 10

<210> SEQ ID NO 35
<211> LENGTH: 18
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 35

Pro Glu Trp Phe Lys Cys Arg Arg Trp Gln Trp Arg Met Lys Lys Leu
1               5                   10                  15

Gly Ala
```